United States Patent [19]

Haigh

[11] Patent Number: 5,589,492
[45] Date of Patent: Dec. 31, 1996

[54] HETEROCYCLIC COMPOUNDS AND THEIR USE IN THE TREATMENT OF TYPE-II DIABETES

[75] Inventor: David Haigh, Horsham, England

[73] Assignee: SmithKline Beecham PLC, Brentford, England

[21] Appl. No.: 318,615

[22] PCT Filed: Apr. 7, 1993

[86] PCT No.: PCT/GB93/00735

§ 371 Date: Dec. 12, 1994

§ 102(e) Date: Dec. 12, 1994

[87] PCT Pub. No.: WO93/21166

PCT Pub. Date: Oct. 28, 1993

[30] Foreign Application Priority Data

| Apr. 10, 1992 | [GB] | United Kingdom | 9208016 |
| Apr. 16, 1992 | [GB] | United Kingdom | 9208451 |
| Dec. 29, 1992 | [GB] | United Kingdom | 9227046 |

[51] Int. Cl.$^6$ .............. C07D 413/12; C07D 213/74; A61K 31/42; A61K 31/44
[52] U.S. Cl. .............. 514/339; 514/347; 514/274; 514/275; 514/375; 544/318; 544/332; 546/271.7; 546/294; 546/301; 546/334; 548/222
[58] Field of Search ............... 544/318, 332; 546/294, 301, 334, 271.7; 548/321, 222; 514/274, 275, 347, 349, 375

[56] References Cited

FOREIGN PATENT DOCUMENTS

| 0306228 | 3/1989 | European Pat. Off. . |
| 92/02520 | 2/1992 | WIPO . |

OTHER PUBLICATIONS

Takashi Sohda, et al., Chemical and Pharmaceutical Bulletin, vol. 30, No. 10, pp. 3563–3573 (1982).
Takashi Sohda, et al., Chemical and Pharmaceutical Bulletin, vol. 30, No. 10, pp. 3580–3600 (1982).

*Primary Examiner*—Zinna Northington-Davis
*Attorney, Agent, or Firm*—Nora Stein-Fernandez; William T. King; Edward T. Lentz

[57] ABSTRACT

A compound of the formula $A^1-X-(CH_2)_n-O-A^2-A^3-CO.R^2$ (I) or a tautomeric form thereof and/or a pharmaceutically acceptable salt thereof, and/or a pharmaceutically acceptable solvate thereof, wherein: $A^1$ represents a substituted or unsubstituted aromatic heterocyclyl group; $A^2$ represents a benzene ring having three optional substituents; $A^3$ represents a moiety of formula $-(CH_2)_m-CHR^1-$ wherein $R^1$ represents a halogen atom or a moiety of formula $S(O)_pA^4$ wherein $A^4$ represents hydrogen, substituted or unsubstituted alkyl, aryl, aralkyl, alkylcarbonyl or an aromatic heterocyclyl group and p represents zero or an integer 1 or 2 and m represents zero or an integer in the range of from 1 to 5, or $A^3$ represents a moiety of formula $-CH=CR^1-$ wherein $R^1$ is as defined above; $R^2$ represents $OR^3$ wherein $R^3$ represents hydrogen, alkyl, aryl or aralkyl, or $R^2$ represents $-NR^4R^5$ wherein $R^4$ and $R^5$ each independently represent hydrogen or alkyl or $R^4$ and $R^5$ together with the nitrogen atom to which they are attached form a heterocyclic ring; X represents O, S or NR wherein R represents a hydrogen atom, an alkyl group, an acyl group, an aralkyl group wherein the aryl moiety may be substituted or unsubstituted, or a substituted or unsubstituted aryl group; and n represents an integer in the range of from 2 to 6; a process for the preparation of such a compound, a pharmaceutical composition comprising such a compound and the use of such a compound and composition in medicine.

12 Claims, No Drawings

HETEROCYCLIC COMPOUNDS AND THEIR USE IN THE TREATMENT OF TYPE-II DIABETES

This application is a 371 of PCT/GB/93/00735 filed Apr. 7, 1993 and published as WO93/21166 Oct. 28, 1993.

This invention relates to certain novel compounds, to a process for preparing such compounds, to pharmaceutical compositions containing such compounds and to the use of such compounds and compositions in medicine.

European Patent Applications, Publication Numbers 0008203, 0139421, 155845, 0177353, 0193256, 0207581, 0208420, 0306228 and International Patent Application Publication No. WO 9101337 relate to thiazolidinedione derivatives which are disclosed as having hypoglycaemic and hypolipidaemic activity. Chem. Pharm. Bull 1982, 30 (10) 3580–3600 relates to certain thiazolidinedione derivatives having hypoglycaemic and hypolipidaemic activities. Chem. Pharm. Bull 1982, 30 (10) 3563 also relates to certain ethyl 2-chloro propionate derivatives having hypoglycaemic and hypolipidaemic activities.

It has now surprisingly been discovered that certain novel α-thiocarbonyl and α-halocarbonyl derivatives show good blood-glucose lowering activity and are therefore of potential use in the treatment and/or prophylaxis of hyperglycaemia and are of particular use in the treatment of Type II diabetes.

These compounds are also indicated to be of potential use for the treatment and/or prophylaxis of other diseases including hyperlipidaemia, hypertension, cardiovascular disease and certain eating disorders.

Accordingly, the present invention provides a compound of formula (I):

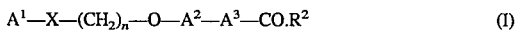

$$A^1—X—(CH_2)_n—O—A^2—A^3—CO.R^2 \quad (I)$$

or a tautomeric form thereof and/or a pharmaceutically acceptable salt thereof, and/or a pharmaceutically acceptable solvate thereof, wherein:

$A^1$ represents a substituted or unsubstituted aromatic heterocyclyl group;
$A^2$ represents a benzene ring having three optional substituents;
$A^3$ represents a moiety of formula —$(CH_2)_m$—$CHR^1$— wherein $R^1$ represents a halogen atom or a moiety of formula $S(O)_pA^4$ wherein $A^4$ represents hydrogen, substituted or unsubstituted alkyl, aryl, aralkyl, alkylcarbonyl or an aromatic heterocyclyl group and p represents zero or an integer 1 or 2 and m represents zero or an integer in the range of from 1 to 5, or $A^3$ represents a moiety of formula —CH=$CR^1$— wherein $R^1$ is as defined above;
$R^2$ represents $OR^3$ wherein $R^3$ represents hydrogen, alkyl, aryl or aralkyl, or $R^2$ represents —$NR^4R^5$ wherein $R^4$ and $R^5$ each independently represent hydrogen or alkyl or $R^4$ and $R^5$ together with the nitrogen atom to which they are attached form a heterocyclic ring;
X represents O, S or NR wherein R represents a hydrogen atom, an alkyl group, an acyl group, an aralkyl group wherein the aryl moiety may be substituted or unsubstituted, or a substituted or unsubstituted aryl group; and
n represents an integer in the range of from 2 to 6.

Suitable aromatic heterocyclyl groups include substituted or unsubstituted, single or fused ring aromatic heterocyclyl groups comprising up to 4 hetero atoms in each ring selected from oxygen, sulphur or nitrogen.

Favoured aromatic heterocyclyl groups include substituted or unsubstituted single ring aromatic heterocyclyl groups having 4 to 7 ring atoms, preferably 5 or 6 ring atoms.

In particular, the aromatic heterocyclyl group comprises 1, 2 or 3 heteroatoms, especially 1 or 2, selected from oxygen, sulphur or nitrogen.

Suitable values for $A^1$ when it represents a 5-membered aromatic heterocyclyl group include thiazolyl and oxazolyl, especially oxazolyl.

Suitable values for $A^1$ when it represents a 6- membered aromatic heterocyclyl group include pyridyl or pyrimidinyl, especially pyridyl.

A particular pyridyl group is a 2-pyridyl group.

Preferably, $A^1$ represents a moiety of formula (a), (b) or (c):

wherein:

$R^6$ and $R^7$ each independently represents a hydrogen or halogen atom, an alkyl or alkoxy group or a substituted or unsubstituted aryl group or when $R^6$ and $R^7$ are each attached to adjacent carbon atoms, then $R^6$ and $R^7$ together with the carbon atoms to which they are attached form a benzene ring wherein each carbon atom represented by $R^6$ and $R^7$ together may be substituted or unsubstituted; and in the moiety of formula (a)

$X^1$ represents oxygen or sulphur.

Aptly, $A^1$ represents a moiety of the above defined formula (a).

Aptly, $A^1$ represents a moiety of the above defined formula (b).

Aptly, $A^1$ represents a moiety of the above defined formula (c).

In one favoured aspect $R^6$ and $R^7$ together represent a moiety of formula (d):

wherein $R^8$ and $R^9$ each independently represent hydrogen, halogen, substituted or unsubstituted alkyl or alkoxy.

Suitably, $R^8$ and $R^9$ each independently represent hydrogen, halogen, alkyl or alkoxy. Favourably, $R^8$ represents hydrogen. Favourably, $R^9$ represents hydrogen. Preferably, $R^8$ and $R^9$ both represent hydrogen.

In a further favoured aspect $R^6$ and $R^7$ each independently represent hydrogen, alkyl or a substituted or unsubstituted phenyl group and more favourably, $R^6$ and $R^7$ each independently represent hydrogen, alkyl or phenyl.

Preferably, for the moiety of formula (a), $R^6$ and $R^7$ together represent the moiety of formula (d).

Preferably, for the moieties of formula (b) or (c), $R^6$ and $R^7$ both represent hydrogen.

Favoured optional substituents for $A^2$ are selected from the group consisting of halogen, substituted or unsubstituted alkyl and alkoxy.

Favourably, $A^2$ represents a moiety of formula (e):

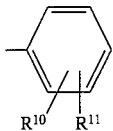

(e)

wherein $R^{10}$ and $R^{11}$ each independently represent hydrogen, halogen, substituted or unsubstituted alkyl or alkoxy.

Suitably, $R^{10}$ and $R^{11}$ each independently represent hydrogen, halogen, alkyl or alkoxy. Preferably, $R^{10}$ and $R^{11}$ each represent hydrogen.

In one aspect, X represents O. In a further aspect, X represents S. In yet a further aspect, and preferably, X represents NR.

Suitably, $A^3$ represents —CH=$CR^1$—. Preferably, $A^3$ represents —$(CH_2)_m$—$CHR^1$.

When $R^1$ represents halogen examples include fluorine, chlorine, bromine and iodine, preferably chlorine.

Preferably, $R^1$ represents a moiety $S(O)_pA^4$.

When $A^4$ represents alkyl, suitable alkyl groups are $C_{1-6}$ alkyl groups such as methyl and propyl; an example is methyl; an example is iso-propyl.

When $A^4$ is substituted alkyl, particular substitutuents for the alkyl group include OH, alkoxy or a moiety —$NR^sR^t$, wherein $R^s$ and $R^t$ each independently represents hydrogen or alkyl or $R^s$ and $R^t$ together with the nitrogen atom to which they are attached form a 5- or 6-membered heterocyclic ring, or a moiety of formula —CO $X^2$ wherein $X^2$ represents OH, alkoxy or a moiety of the above defined formula —$NR^sR^t$.

Generally when $A^4$ is substituted alkyl, the substituent is attached to a terminal carbon atom of the alkyl group.

An example of a substituted alkyl group represented by $A^4$, includes $(CH_2)_wNR^sR^t$ wherein w is an integer in the range from 2 to 6, preferably 2, and $R^s$ and $R^t$ are as defined above.

When $A^4$ represents aryl, it is generally phenyl. Examples of substituents for aryl groups represented by $A^4$ include alkyl, alkoxy and halogen, for example methyl, methoxy and chloride; phenyl substituents are usually substituted at the 4-position on the phenyl ring.

When $A^4$ is an aromatic heterocyclic group, suitable groups include those described herein for $A^1$, especially moiety (c), for example 2-pyridyl.

Examples of alkylcarbonyl groups represented by $A^4$ include methylcarbonyl.

Favoured values of $A^4$ include methyl, propyl, an example being iso propyl, phenyl and —$CH_2CH_2NH_2$.

Preferred values of $A^4$ are iso propyl and phenyl.

Suitably, $R^2$ represents $OR^3$. Suitably, $R^2$ represents —$NR^4R^5$ wherein $R^4$ and $R^5$ are as defined above.

Suitably, $R^3$ represents hydrogen or alkyl.

When $R^3$ is alkyl it is suitably $C_{1-6}$ alkyl, for example methyl or ethyl.

Suitably, $R^4$ and $R^5$ each independently represent hydrogen or $C_{1-6}$ alkyl.

When —$NR^4R^5$ or —$NR^sR^t$ represents a heterocyclic ring, favoured heterocyclic tings are saturated or unsaturated, fused or monocyclic heterocyclic rings comprising 5, 6 or 7 ring atoms and optionally comprising 1 or 2 additional heteroatoms, selected from O, S or N, in each ring. Favoured rings are saturated rings. Favoured rings are monocyclic rings. Favoured, additional hetero-atoms are N or O. Examples of such heterocyclic rings include N-pyrrolidinyl, N-piperidinyl and N-morpholinyl.

Further examples of $NR^4R^5$ include $NH_2$ and $N(CH_3)_2$.

Suitably, R represents hydrogen or alkyl.

When R is acyl, suitable acyl groups include acetyl.

Suitably, m represents 1.

Suitably, n represents 2.

Suitably, p represents zero or 2.

Preferably, p represents zero.

As indicated above, a compound of formula (I), and the pharmaceutically acceptable salts thereof, may exist in one of several tautomeric forms, all of which are encompassed by the present invention as individual tautomeric forms or as mixtures thereof. The compounds of formula (I) may contain at least one chiral carbon, and hence they may exist in one or more stereoisomeric forms. For example, the $CHR^1$-carbon atom is a chiral carbon. In addition, when $A^3$ represents a moiety of formula —CH=$CR^1$— the compounds of formula (I) exist as geometric isomers. The present invention encompasses all of the stereoisomeric forms of the compounds of formula (I) and the pharmaceutically acceptable salts thereof, whether as individual stereoisomers or as mixtures of isomers, including racemates.

Suitable substituents for any heterocyclyl group include up to 4 substituents selected from the group consisting of: alkyl, alkoxy, aryl and halogen or any two substituents on adjacent carbon atoms, together with the carbon atoms to which they are attached, may form an aryl group, preferably a phenylene group, and wherein the carbon atoms of the aryl group represented by the said two substituents may themselves be substituted or unsubstituted.

When used herein, unless otherwise stated, the term 'aryl' includes phenyl and naphthyl; any aryl group mentioned herein may be optionally substituted with up to five, preferably up to three, groups selected from halogen, alkyl, phenyl, alkoxy, haloalkyl, hydroxy, amino, nitro, carboxy, alkoxycarbonyl, alkoxycarbonylalkyl, alkylcarbonyloxy, or alkylcarbonyl groups.

When used herein the term 'halogen' refers to fluorine, chlorine, bromine and iodine; preferably chlorine.

As used herein, alkyl groups, whether present alone or as pan of other groups, such as alkoxy, aralkyl or alkylcarbonyl groups, are alkyl groups having straight or branched carbon chains, containing up to 12 carbon atoms. Thus, suitable alkyl groups are $C_{1-12}$ alkyl groups, especially $C_{1-6}$ alkyl groups e.g. methyl, ethyl, n-propyl, iso-propyl, n-butyl, isobutyl or tert-butyl groups.

Suitable substituents for any alkyl group include those indicated above in relation to the term "aryl".

Suitable acyl groups include alkylcarbonyl groups.

Suitable pharmaceutically acceptable salts include salts of carboxy groups and acid addition salts.

Suitable pharmaceutically acceptable salts of carboxy groups include metal salts, such as for example aluminium, alkali metal salts such as lithium, sodium or potassium, alkaline earth metal salts such as calcium or magnesium and ammonium or substituted ammonium salts, for example those with lower alkylamines such as triethylamine, hydroxy alkylamines such as 2-hydroxyethylamine, bis-(2-hydroxyethyl)-amine or tri-(2-hydroxyethyl)-amine, cycloalkylamines such as bicyclohexylamine, or with procaine, dibenzylpiperidine, N-benzyl-β-phenethylamine, dehydroabietylamine, N,N'-bisdehydroabietylamine, glucamine, N-methylglucamine or bases of the pyridine type such as pyridine, collidine, quinine or quinoline.

Suitable acid addition salts include pharmaceutically acceptable inorganic salts such as the sulphate, nitrate, phosphate, borate, hydrochloride and hydrobromide and pharmaceutically acceptable organic acid addition salts such as acetate, tartrate, maleate, citrate, succinate, benzoate, ascorbate, methane-sulphonate, α-keto glutarate and α-glycerophosphate.

Suitable pharmaceutically acceptable solvates include hydrates.

In a further aspect the present invention also provides a process for the preparation of a compound of formula (I), or a tautomeric form thereof, and/or a pharmaceutically acceptable salt thereof, and/or a pharmaceutically acceptable hydrate thereof, which process comprises reacting a compound of formula (II):

$$R^a\text{—}A^2\text{—}A^3\text{—}CO.R^2 \qquad \text{(II)}$$

wherein $R^1$, $R^2$, $A^2$ and $A^3$ are as defined in relation to formula (I) and $R^a$ is a moiety convertible to a moiety of formula (f):

$$A^1\text{—}X\text{—}(CH_2)_n\text{—}O\text{—} \qquad \text{(f)}$$

wherein $A^1$, X and n are as defined in relation to formula (I), with an appropriate reagent capable of converting $R^a$ to the said moiety (f) and thereafter, if required, carrying out one or more of the following optional steps:

(i) converting a compound of formula (I) to a further compound of formula (I);

(ii) removing any necessary protecting group;

(iii) preparing a pharmaceutically acceptable salt of the compound of formula (I) and/or a pharmaceutically acceptable solvate thereof.

Suitably, $R^a$ represents HX—$(CH_2)_n$—O— wherein X and n are as defined in relation to formula (I), or $R^a$ represents OH.

Preferably, Ra represents OH.

When $R^a$ is HX—$(CH_2)_n$—O—, an appropriate reagent capable of converting $R^a$ to a moiety (f) is a compound of formula (III):

$$A^1\text{—}R^x \qquad \text{(III)}$$

wherein $A^1$ is as defined in relation to formula (I) and $R^x$ represents a leaving group.

A suitable leaving group $R^x$ includes a halogen atom, preferably a chlorine or bromine atom, or a thioalkyl group for example a thiomethyl group.

When Ra is OH, an appropriate reagent is a compound of formula (IIIA):

$$A^1\text{—}X\text{—}(CH_2)_n\text{—}OR^y \qquad \text{(IIIA)}$$

wherein $A^1$, X and n are as defined in relation to formula (I) and $R^y$ represents a leaving group, such as a rosylate or mesylate group.

The reaction between the compound of formula (II) and the appropriate reagent may be carried out under conditions suitable to the particular compound of formula (II) and the reagent chosen: For example the abovementioned reaction between a compound of formula (II) wherein $R^a$ represents HX—$(CH_2)_n$—O— and the compound of formula (III), may be carried out in any suitable solvent, for example dimethylformamide, at a temperature which provides a suitable rate of formation of the compound of formula (I), for example at an elevated temperature in the range from 50° C. to 120° C., preferably in the presence of a base such as sodium hydride.

When $R^y$ in the reagent of formula (IIIA) represents a leaving group, such as a tosylate or mesylate group, the reaction between the compound of formula (IIIA) and the compound of formula (II) wherein $R^a$ is OH may be carried out in an aprotic solvent, such as dimethylformamide, at a low to an elevated temperature, for example in the range from 50° C. to 120° C., for example at 80° C., and preferably in the presence of a base, such as sodium hydride.

When $R^y$ in the reagent of formula (IIIA) represents a hydrogen atom, the reaction between the compound of formula (IIIA) and the compound of formula (II) wherein $R^a$ is OH is conveniently carried out in the presence of a suitable coupling agent; a suitable coupling agent being provided by diethylazodicarboxylate and triphenylphosphine. The coupling reaction may be carried out in any suitable solvent at a low to medium temperature, for example in tetrahydrofuran at a temperature in the range of between 0° and 60° C., conveniently at ambient temperature.

A compound of formula (II), wherein $A^3$ represents a moiety of formula —$(CH_2)_m$—$CHR^1$— wherein $R^1$ represents the above defined moiety $S(O)_pA^4$ and m is as defined in relation to formula (I), may be prepared by reacting a compound of formula (IV):

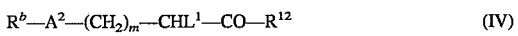

$$R^b\text{—}A^2\text{—}(CH_2)_m\text{—}CHL^1\text{—}CO\text{—}R^{12} \qquad \text{(IV)}$$

wherein $A^2$ and m are as defined in relation to the compound of formula (I), $R^b$ is a moiety $R^a$ or a moiety convertible to a moiety $R^a$, $R^{12}$ is $R^2$ or a protected form thereof and $L^1$ is a halogen atom, with an activated form of a compound of formula (V):

$$R^1S(O)_pH \qquad \text{(V)}$$

wherein $R^1$ and p are as defined in relation to formula (I); mid thereafter, if required, converting a moiety $R^b$ into a moiety $R^a$ and removing any protecting group.

A suitable halogen atom $L^1$ is a chlorine atom.

Suitably, $R^{12}$ is $R^2$.

A suitable activated form of a compound of formula (V) is an anionic form such as a salted form and especially an alkali metal salted form, for example a sodium salt.

Preferably, in the reaction between the compounds of formulae (IV) and (V) Rb is a protecting group.

The activated form of the compound of formula (V) may be prepared by any appropriate conventional procedure. For example, the anionic form of the compound of formula (V) may be prepared by treating the compound of formula (V) with a base, such as a metal hydride base, for example sodium hydride.

A compound of formula (II), wherein $A^3$ represents a moiety of formula —$(CH_2)_m$—$CHR^1$— wherein $R^1$ represents a halogen atom and m is as defined in relation to formula (I), may be prepared from a compound of formula (IV) by converting $R^b$ into $R^a$ and $R^{12}$ into $R^2$, as necessary.

A compound of formula (IV) may be prepared by halogenating a compound of formula (VI):

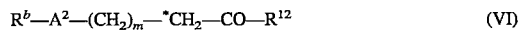

$$R^b\text{—}A^2\text{—}(CH_2)_m\text{—}^*CH_2\text{—}CO\text{—}R^{12} \qquad \text{(VI)}$$

wherein $A^2$, $R^{12}$, m and $R^b$ are as defined in relation to the compound of formula (IV), with an appropriate halogenating agent; and thereafter, if required, converting a moiety $R^b$ into a moiety $R^a$ and removing any protecting group.

Preferably, the compound of formula (VI) is in an activated form, in particular it is preferred if the —*CH$_2$— carbon atom is an activated carbon atom.

A suitable activated form of a compound of formula (VI) is an ionic form, in particular an anionic form.

The activated form of the compound of formula (VI) may be prepared by any appropriate conventional procedure. For example, the anionic form of the compound of formula (VI) may be prepared by treating the compound of formula (VI) with a base such as a metal hydride base, for example sodium hydride, or a metal amide base, for example a lithium amide base. One preferred base is the lithium amide, lithium diisopropylamide. The lithium amide base is preferably used in the presence of a chlorosilane such as chlorotrimethylsilane.

The reaction conditions for the halogenation of the compound of formula (VI) and the nature of the halogenating agent used are analogous to the conditions used and the reagent used for halogenation reactions discussed hereinafter.

In the above mentioned reactions any moiety $R^b$ may be convened into a moiety $R^a$ by the appropriate conventional means, for example when $R^b$ represents —OH and $R^a$ represents HX—(CH$_2$)$_n$—O— the appropriate conversion may be carried out by coupling a compound wherein $R^b$ is OH with a compound of formula (g):

$$R^z-X-(CH_2)_n-OH \qquad (g)$$

wherein X and n are as defined in relation to formula (I) and $R^z$ is a protecting group and thereafter, if necessary, removing any protecting group.

The last abovementioned reaction is generally carried out in the presence of a suitable coupling agent; a suitable coupling agent being diethylazodicarboxylate and triphenylphosphine. The coupling reaction may be carried out in any suitable solvent at a low to medium temperature, for example in tetrahydrofuran at a temperature in the range of between 0° and 60° C.

Generally, for compounds of formula (IV) wherein $R^a$ is OH, $R^b$ is either OH or a protected OH, such as a benzylated OH.

The compounds of formulae (V) and (VI) are known compounds or they may be prepared using methods analogous to those used to prepare known compounds, in particular the compounds wherein $R^b$ is OH, m is 1 and $R^{12}$ is OH are commercially available compounds. The compounds wherein $R^{12}$ is protected OH may of course be prepared by appropriate protection procedures.

The compounds of formula (g), are known compounds or they may be prepared using methods analogous to those used to prepare known compounds, for example those disclosed in EP0356214.

A compound of formula (I), wherein $A^3$ represents a moiety of formula —(CH$_2$)$_m$—CHR$^1$— wherein $R^1$ represents the above defined moiety S(O)$_p$A$^4$ and m is as defined in relation to formula (I), or a tautomeric form thereof, and/or a pharmaceutically acceptable salt thereof and/or a pharmaceutically acceptable solvate thereof, may also be prepared by reacting a compound of formula (VII):

$$A^1-X-(CH_2)_n-O-A^2-(CH_2)_m-CHL^2-CO-R^{12} \qquad (VII)$$

wherein $A^1$, $A^2$, X, m and n are as defined in relation to formula (I), $R^{12}$ is as defined in relation to formula (IV) and $L^2$ represents a leaving group, with a compound of the above defined formula (V); and thereafter if required carrying out one or more of the following optional steps:

(i) converting a compound of formula (I) into a further compound of formula (I);

(ii) removing any protecting group; and (iii) preparing a pharmaceutically acceptable salt of a compound of formula (I) and/or a pharmaceutically acceptable solvate thereof.

Suitably, $L^2$ represents a halogen atom, generally a chlorine atom.

The reaction conditions for the reaction between the compounds of formulae (V) and (VII) are analogous to the conditions described herein for the reaction between the compounds of formulae (IV) and (V).

A compound of formula (I) wherein $A^3$ represents a moiety of formula (CH$_2$)$_m$—CHR$^1$— wherein $R^1$ represents a halogen atom, or a tautomeric form thereof, and/or a pharmaceutically acceptable salt thereof and/or a pharmaceutically acceptable solvate thereof, may be prepared by deprotecting a compound of formula (VII) wherein $R^{12}$ is a protected form of $R^2$ and $L^2$ is halogen; and thereafter if required carrying out one or more of the following optional steps:

(i) converting a compound of formula (I) into a further compound of formula (I); and (ii) preparing a pharmaceutically acceptable salt of a compound of formula (I) and/or a pharmaceutically acceptable solvate thereof.

The deprotection step may be carried out using the appropriate conventional procedure.

A compound of formula (I) wherein $A^3$ represents a moiety of formula (CH$_2$)$_m$—CHR$^1$— wherein $R^1$ represents a halogen atom, or a tautomeric form thereof, and/or a pharmaceutically acceptable salt thereof and/or a pharmaceutically acceptable solvate thereof, may also be prepared by halogenating a compound of formula (VIII):

$$A^1-X-(CH_2)_n-O-A^2-(CH_2)_m-^*CH_2-CO-R^{12} \qquad (VIII)$$

wherein $A^1$, $A^2$, $R^{12}$, X, m and n are as defined in relation to formula (VII), with an appropriate halogenating agent, and thereafter if required carrying out one or more of the following optional steps:

(i) converting a compound of formula (I) into a further compound of formula (I);

(ii) removing any protecting group; and (iii) preparing a pharmaceutically acceptable salt of a compound of formula (I) and/or a pharmaceutically acceptable solvate thereof.

Preferably, the compound of formula (VIII) is in an activated form, in particular it is preferred if the —*CH$_2$— carbon atom is an activated carbon atom.

A suitable activated form of a compound of formula (VIII) is an ionic form, in particular an anionic form.

The activated form of the compound of formula (VIII) may be prepared by any appropriate conventional procedure. For example, the anionic form of the compound of formula (VIII) may be prepared by treating the compound of formula (VIII) with a base such as a metal hydride base such as sodium hydride, or a metal amide base, such as a lithium amide. One preferred base is the lithium amide, lithium diisopropylamide. The lithium amide base is preferably used in the presence of a chlorosilane such as chlorotrimethylsilane.

Appropriate halogenating agents are conventional halogenating agents capable of halogenating the —*CH$_2$— carbon atom without disrupting the rest of the substrate molecule, one particular agent is an N-halosuccinimide such as N-chlorosuccinimide.

The reaction between the activated form of a compound of formula (VIII) and the halogenating agent may be carried out under the conditions necessitated by the particular nature of the compound of formula (VIII) and the halogenating agent used: for example, when an N-halosuccinimide is used as the halogenating agent, the reaction may be carried out in an aprotic solvent, such as tetrahydrofuran, preferably dry tetrahydrofuran, at a temperature which provides a suitable rate of formation of the required product, being generally a low temperature, for example in the range of from −90° to 10° C.; and preferably the reaction is carried out under an inert atmosphere.

A compound of formula (VII) may also be prepared from a compound of the above formula (VIII) by reacting with a reagent capable of forming the group $L^2$, for example when $L^2$ is a halogen atom, by reaction with an appropriate halogenating agent, and thereafter, if required, removing any protecting group.

Suitable reagents and reaction conditions are the appropriate conventional reagents such as the halogenating agents/conditions mentioned above.

A compound of formula (VIII) may be prepared by reacting a compound of formula (IX):

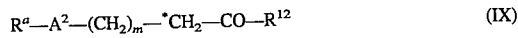

wherein $R^a$, $R^{12}$, $A^2$ and m are as defined above, with an appropriate reagent capable of converting $R^a$ into a moiety of the above defined formula (f).

The reagent capable of converting $R^a$ to a moiety of formula (f) is as defined above in relation to the formation of a compound of formula (I) from a compound of formula (II).

Suitable values for $R^a$ include those described hereinbefore.

Suitable reaction conditions for the reaction of the compound of formula (IX) and the appropriate reagent include those described above in relation to the preparation of compound (II) with the said appropriate reagent.

Preferably, in the compound of formula (IX), $R^a$ represents a hydroxyl group and a particularly appropriate reagent is the above defined compound of formula (IIIA).

The reaction between the compound of formula (IX), wherein $R^a$ is an hydroxyl group, and the reagent of the abovedefined formula (IIIA) may be carried out in an aprotic solvent, such as dimethylformamide, at a low to an elevated temperature, for example in the range of from 50° C. to 120° C., for example at 80° C., and preferably in the presence of a base, such as sodium hydride.

A compound of formula (VIII), wherein m is other than zero, may also be prepared by reducing a compound of formula (X):

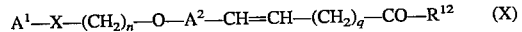

wherein $A^1$, $A^2$, $R^{12}$, X and n are as defined in relation to formula (VII), and q is zero or an integer 1, 2, 3, or 4 and thereafter, if required, removing any protecting group.

The reduction of a compound of formula (X) may be effected by standard reduction methods, for example by catalytic reduction using platinum (IV) oxide catalyst and hydrogen.

A compound of formula (X) may be prepared by reacting a compound of formula (XI):

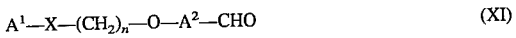

wherein $A^1$, $A^2$, X and n are as defined in relation to formula (X), with a reagent capable of forming a moiety CH=CH—$(CH_2)_q$—CO—$R^{12}$ from the —CHO group.

A suitable reagent capable of converting the CHO carbon atom into a group of the above defined formula CH=CH—$(CH_2)_q$—CO—$R^{12}$ is a Wittig reagent of formula (XII):

wherein $R^{12}$ and q are as defined in relation to the compound of formula (X) and $M^-$ is a counter-ion, suitably a halogen, for example chloride or bromide.

The abovementioned reaction between the compound of formula (XI) and the said reagent may be carried out under conventional conditions depending upon the particular nature of the reagent used: for example the reaction between a compound of formula (XI) and the Wittig reagent of formula (XII) may be carried out under conventional Wittig reaction conditions, for example in an aprotic solvent, such as tetrahydrofuran or, preferably, dimethyl sulphoxide, at low to ambient temperature, such as in the range of from −10° to 25° C. generally at 0°–10° C. The reaction is most effectively carried out under an inert atmosphere and under anhydrous conditions. Preferably, the Wittig reagent is activated prior to addition of the compound of formula (XI) by addition of a base such as sodium hydride.

For compounds of formula (X) wherein q is zero, the reagent is preferably a Wadsworth Emmons reagent of formula (XIIA):

wherein $R^{12}$ is as defined in relation to formula (X) and $R^{13}$ represents a $C_{1-6}$ alkyl group, preferably a methyl or ethyl group, for example for compounds of formula (X) wherein $R^{13}$ is methoxy, the Wadsworth Emmons reagent of formula (XIIA) is trimethyl phosphonoacetate.

The reaction between a compound of formula (XI) and the Wadsworth Emmons reagent of formula (XIIA) may be carried out under conventional Wadsworth Emmons reaction conditions, for example in an aprotic solvent, such as tetrahydrofuran, at low to ambient temperature, such as in the range of from −10° to 25° C. generally at 0°–10° C., and preferably in the presence of a base such as sodium hydride. The reaction is most effectively carried out under an inert atmosphere and under anhydrous conditions. Preferably, the trimethyl phosphonoacetate is activated prior to addition of the compound of formula (XI) by addition of a base such as sodium hydride.

A compound of formula (I) or a tautomeric form thereof and/or a pharmaceutically acceptable salt thereof, and/or a pharmaceutically acceptable solvate thereof, may be prepared by reacting a compound of the above defined formula (XI), with a reagent capable of forming a moiety —$A^{3'}$—CO—$R^2$ from the —CHO group wherein $A^{3'}$ is —CH=$CR^1$—, wherein $R^1$ is as described above and r is an integer 1 to 3; and thereafter if required carrying out one or more of the following optional steps:

(i) reducing the compound so formed;
(ii) converting a compound of formula (I) into a further compound of formula (I);
(iii) removing any protecting group; and
(iv) preparing a pharmaceutically acceptable salt of a compound of formula (I) and/or a pharmaceutically acceptable solvate thereof.

A suitable reagent capable of converting the CHO carbon atom into a group of the above defined formula —A³—CO—R² is a Wittig reagent of formula (XIII):

[Ph₃P—CHR¹CO—R¹²]⁺M⁻ (XIII)

wherein R¹ and m are as defined on relation to formula (I) and R¹² and M are as defined in relation to formula (XII).

The abovementioned reaction between the compound of formula (XI) and the said reagent may be carried out under conventional conditions depending upon the particular nature of the reagent used: for example the reaction between a compound of formula (XI) and the Wittig reagent of formula (XIII) may be carried out under conventional Wittig reaction conditions, for example in an aprotic solvent, such as tetrahydrofuran or, preferably, dimethyl sulphoxide, at low to ambient temperature, such as in the range of from −10° to 25° C. generally at 0°–10° C., and preferably in the presence of a base such as sodium hydride. The reaction is most effectively carried out under an inert atmosphere and under anhydrous conditions. Preferably, the Wittig reagent is activated prior to addition of the compound of formula (XI) by addition of a base such as sodium hydride.

However, for compounds of formula (I) wherein A³ is —CH=CR¹— or —CH₂—CHR¹—, it is preferred if the reagent is a Wadsworth Emmons reagent of formula (XIIIA):

$$(R^{13}O)_2\overset{O}{\underset{\|}{P}}-CHR^1-CO.R^{12}$$ (XIIIA)

wherein R¹ is as defined in relation to formula (I) and and R¹² are R¹³ are as defined in relation to formula (XIIA); for example, for compounds of formula (I), wherein R¹ is fluorine and R² is ethyl, a suitable Wadsworth Emmons reagent is triethyl 2-fluorophosphonoacetate.

The reaction between the compound of formula (XI) and the Wadsworth Emmons reagent may be carried as described herein before for the reaction between the compounds of formulae (XI) and XIIA).

The reduction (i) may be effected by standard reduction methods, for example by catalytic reduction using platinum (IV) oxide catalyst or a 10% palladium on carbon catalyst and hydrogen, in any suitable solvent such as an alkanolic solvent, for example ethanol.

A compound of formula (II) wherein A³ represents a moiety of formula —CH=CH— or —(CH₂)₂— may be prepared by reacting a compound of formula (XIV):

Rᵇ—A²—CHO (XIV)

wherein A² and Rᵇ are as defined in relation to the compound of formula (II); with a compound of the above defined formula (XII), or preferably (XIIA), to provide a compound of formula (II) wherein A³ represents a moiety of formula —CH=CH—, which thereafter, if required, may be reduced to provide a compound wherein A³ represents a moiety of formula —CH₂—CH₂—.

The reaction conditions for the reaction between the compounds of formulae (XII) or (XIIA) and (XIV) are analogous to those used in the reaction between the compounds of formulae (XI) and (XII) or (XIIA).

The present invention also provides a process for preparing a compound of formula (I) wherein A³ represents a moiety of formula —(CH₂)ₘ—CHR¹— wherein R¹ represents the above defined moiety S(O)ₚA⁴ and m is as defined in relation to formula (I), or a tautomeric form thereof, and/or a pharmaceutically acceptable salt thereof and/or a pharmaceutically acceptable solvate thereof, which process comprises hydrolysing a compound of formula (XV):

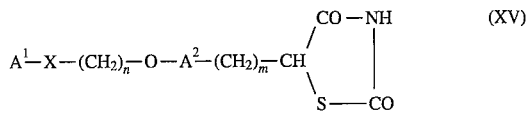

$$A^1-X-(CH_2)_n-O-A^2-(CH_2)_m-CH\begin{matrix}CO-NH\\ |\\ S-CO\end{matrix}$$ (XV)

wherein A¹, A², X, m and n are as defined in relation to formula (I) to provide a compound of formula (I) wherein R¹ is SH and R² is OH; and thereafter, if required, carrying out one or more of the following optional steps:

(i) converting a compound of formula (I) into a further compound of formula (I), in particular converting R¹ is SH into another R¹ and/or converting R² is OH into another R²;

(ii) removing any protecting group; and (iii) preparing a pharmaceutically acceptable salt of a compound of formula (I) and/or a pharmaceutically acceptable solvate thereof.

Preferably in the compound of formula (XV), m is 1.

Suitable hydrolysis conditions are conventional conditions and include basic hydrolysis using, for example, an alkali metal base such as sodium hydroxide in any suitable solvent, generally an aqueous solvent, at a temperature providing a convenient rate of formation of the required product, generally at an elevated temperature such as the reflux temperature of the solvent, and preferably under an inert atmosphere.

Suitable conversions of R¹ as SH into another R¹ and/or R² as OH into another R² may be carried out under the appropriate conventional conditions such as those described hereinafter.

The compounds of formula (IX), wherein Rᵃ is OH, are known compounds or they are compounds prepared by methods analogous to those used to prepare known compounds, for example those disclosed in Dictionary of Organic Compounds 5th Edition, Vol. 3, p.3222, Chapman & Hall, or D. H. Williams et. al. J. Chem. Soc., Section B, 1969, 439, or J. March, Advanced Organic Chemistry, 3rd Edition (1985), Wiley Interscience.

The compounds of formulae (XII), (XIIA), (XIII) and (XIIIA) are known compounds or they may be prepared according to methods used to prepare known compounds, for example those disclosed in J. Amer. Chem. Soc. 1961, 83, 1733, Synlett. 1991, 517 or J. Org. Chem. 1990,55, 4639.

The compounds of formula (III), (IIIA), (XI), (XIV) and (XV) are known compounds or they are prepared according to methods used to prepare known compounds, for example those methods disclosed in EP 0306228.

The abovementioned conversion of a compound of formula (I) into a further compound of formula (I) includes:

a) converting one group R into another group R;

b) converting one group S(O)p.R¹ into another group S(O)p.R¹; and c) converting one group CO.R² into another group CO.R².

d) reducing A³ as —CH=CH— to provide—(CH₂)₂—

The abovementioned conversions may as appropriate be carried out on any of the intermediate compounds mentioned herein.

The conversion of a compound of formula (I) to a further compound of formula (I) may be carried out by using any appropriate conventional procedure.

Suitable conversions of one group R into another group R include converting a group R which represents hydrogen into a group R which represents an acyl group; such conversion may be carried out using an appropriate conventional acylation procedure, for example treating an appropriately protected compound of formula (I) with an acylating agent. Thus acetic anhydride may be used to prepare the compound of formula (I) wherein R is acetyl.

Suitable conversions of one group $S(O)p.R^1$ into another group $S(O)p.R^1$ include converting a group $S(O)p.R^1$ wherein p is zero into a group wherein p is 2, such conversion may be carried out using an appropriate conventional oxidation procedure, for example treating an appropriately protected compound of formula (I) with an oxidising agent such as monoperoxyphthalic acid, preferably salted as a magnesium salt.

Suitable conversions of one group $CO.R^2$ into another group $CO.R^2$ include:

(i) hydrolysing one group $CO.R^{2a}$ wherein $R^{2a}$ is alkyl, aryl or aralkyl into a group CO.OH; and (ii) aminating one group $CO.R^{2b}$ wherein $R^{2b}$ is alkoxy into a group $CO.NR^4R^5$ wherein $R^4$ and $R^5$ are as defined in relation to formula(I)..

Suitable hydrolysis methods for use in conversion c (i) are conventional ester hydrolysis methods, for example using an alkali hydroxide in aqueous methanol.

Suitable amination methods for conversion c (ii) include conventional methods, for example treatment with aqueous ammonia in tetrahydrofuran/methanol or treatment with an appropriate dialkylamine in a solvent such as tetrahydrofuran/methanol.

Suitable reductions of $A^3$ as —CH=CH— to provide —(CH$_2$)$_2$— are carried out using conventional reducing methods, such as those described herein.

It will be appreciated that in any of the abovementioned reaction including the abovementioned conversions (a),(b), (c) and (d) any reactive group in the substrate molecule may be protected, according to conventional chemical practice.

In the abovementioned procedures protecting groups will be used when and as necessary in accordance with conventional procedures.

Suitable protecting groups in any of the abovementioned reactions are those used conventionally in the art. Thus, for example, a suitable hydroxyl protecting group is a benzyl group.

The methods of formation and removal of such protecting groups are those conventional methods appropriate to the molecule being protected. Thus for example a benzyloxy group may be prepared by treatment of the appropriate compound with a benzyl halide, such as benzyl bromide, and thereafter, if required, the benzyl group may be conveniently removed using catalytic hydrogenation or a mild ether cleavage reagent such as trimethylsilyl iodide or boron tribromide.

In the preparation of compounds comprising a moiety of formula (h):

(h)

wherein $R^1$ represents a substituted alkyl wherein the substituent is a moiety of the above defined formula $X^1NR^3R^t$, wherein $X^1$ is a bond (and in particular when $R^1$ is $(CH_2)_2NH_2$), $R^2$ is OH and p is zero, it is generally found convenient to protect the said moiety (h) as a thiazine-3-one and to remove such protection by treating with a base, such as aqueous sodium hydroxide.

Where appropriate the isomeric forms of the compounds of formula (I) and the pharmaceutically acceptable salts thereof may be prepared as individual isomers using conventional chemical procedures.

As mentioned above the compounds of the invention are indicated as having useful therapeutic properties: The present invention accordingly provides a compound of formula (I), or a tautomeric form thereof and/or a pharmaceutically acceptable salt thereof and/or a pharmaceutically acceptable solvate thereof, for use as an active therapeutic substance.

Thus the present invention provides a compound of formula (I), or a tautomeric form thereof and/or a pharmaceutically acceptable salt thereof and/or a pharmaceutically acceptable solvate thereof, for use in the treatment of and/or prophylaxis of hyperglycaemia.

In a further aspect the present invention also provides a compound of formula (I), or a tautomeric form thereof and/or a pharmaceutically acceptable salt thereof and/or a pharmaceutically acceptable solvate thereof, for use in the treatment and/or prophylaxis of hyperlipidaemia.

As indicated hereinbefore the present invention also provides a compound of formula (I) or a tautomeric form thereof and/or a pharmaceutically acceptable salt thereof and/or a pharmaceutically acceptable solvate thereof for use in the treatment of hypertension, cardiovascular disease and certain eating disorders.

A compound of formula (I), or a tautomeric form thereof and/or a pharmaceutically acceptable salt thereof and/or a pharmaceutically acceptable solvate thereof, may be administered per se or, preferably, as a pharmaceutical composition also comprising a pharmaceutically acceptable carrier.

Accordingly, the present invention also provides a pharmaceutical composition comprising a compound of the general formula (I), or a tautomeric form thereof, or a pharmaceutically acceptable salt thereof, or a pharmaceutically acceptable solvate thereof, and a pharmaceutically acceptable carrier therefor.

As used herein the term 'pharmaceutically acceptable' embraces compounds, compositions and ingredients for both human and veterinary use: for example the term 'pharmaceutically acceptable salt' embraces a veterinarily acceptable salt.

The composition may, if desired, be in the form of a pack accompanied by written or printed instructions for use.

Usually the pharmaceutical compositions of the present invention will be adapted for oral administration, although compositions for administration by other routes, such as by injection and percutaneous absorption are also envisaged.

Particularly suitable compositions for oral administration are unit dosage forms such as tablets and capsules. Other fixed unit dosage forms, such as powders presented in sachets, may also be used.

In accordance with conventional pharmaceutical practice the carrier may comprise a diluent, filler, disintegrant, wetting agent, lubricant, colourant, flavourant or other conventional adjuvant.

Typical carriers include, for example, microcrystalline cellulose, starch, sodium starch glycollate, polyvinylpyrrolidone, polyvinylpolypyrrolidone, magnesium stearate or sodium lauryl sulphate.

Most suitably the composition will be formulated in unit dose form. Such unit dose will normally contain an amount of the active ingredient in the range of from 0.1 to 1000 mg, more usually 0.1 to 500 mg, and more especially 0.1 to 250 mg.

The present invention further provides a method for the treatment and/or prophylaxis of hyperglycaemia in a human or non-human mammal which comprises administering an effective, non-toxic, amount of a compound of the general formula (I), or a tautomeric form thereof and/or a pharmaceutically acceptable salt thereof and/or a pharmaceutically acceptable solvate thereof to a hyperglycaemic human or non-human mammal in need thereof.

The present invention further provides a method for the treatment of hyperlipidaemia in a human or non-human mammal, which comprises administering an effective, non-toxic, amount of a compound of formula (I), or a tautomeric form thereof and/or a pharmaceutically acceptable salt thereof and/or a pharmaceutically acceptable solvate thereof, to a hyperlipidaemic human or non-human mammal in need thereof.

Conveniently, the active ingredient may be administered as a pharmaceutical composition hereinbefore defined, and this forms a particular aspect of the present invention.

In the treatment and/or prophylaxis of hyperglycaemic humans, and/or the treatment and/or prophylaxis of hyperlipidaemic human, the compound of the general formula (I), or a tautomeric form thereof and/or a pharmaceutically acceptable salt thereof and/or a pharmaceutically acceptable solvate thereof, may be taken in doses, such as those described above, one to six times a day in a manner such that the total daily dose for a 70 kg adult will generally be in the range of from 0.1 to 6000 mg, and more usually about 1 to 1500 mg.

In the treatment and/or prophylaxis of hyperglycaemic non-human mammals, especially dogs, the active ingredient may be administered by mouth, usually once or twice a day and in an amount in the range of from about 0.025 mg/kg to 25 mg/kg, for example 0.1 mg/kg to 20 mg/kg. Similar dosage regimens are suitable for the treatment and/or prophylaxis of hyperlipidaemia in non-human mammals.

The dosages regimens for the treatment of hypertension, cardiovascular disease and eating disorders will generally be those mentioned above in relation to hyperglycaemia.

In a further aspect the present invention provides the use of a compound of formula (I), or a tautomeric form thereof and/or a pharmaceutically acceptable salt thereof and/or a pharmaceutically acceptable solvate thereof, for the manufacture of a medicament for the treatment and/or prophylaxis of hyperglycaemia.

The present invention also provides the use of a compound of formula (I), or a tautomeric form thereof and/or a pharmaceutically acceptable salt thereof, and/or a pharmaceutically acceptable solvate thereof, for the manufacture of a medicament for the treatment and/or prophylaxis of hyperlipidaemia, hypertension, cardiovascular disease or certain eating disorders.

No toxicological effects are indicated when a compound of the invention is administered in the above mentioned dosage range.

The following Procedures and Examples illustrate the invention but do not limit it in any way.

EXAMPLE 1

Methyl 3-[4-[2-[N-(2-benzoxazolyl)-N-methylamino]ethoxy]phenyl]-2-chloropropanoate

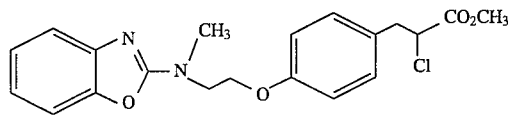

Method A

A solution of lithium diisopropylamide (1.6M, 17.5 mL) was added to a solution of chlorotrimethylsilane (3.6 mL) in dry tetrahydrofuran (100 mL) at −70° C. under a nitrogen atmosphere. A solution of methyl 3-[4-[2-[N-(2-benzoxazolyl)-N-methylamino]ethoxy]phenyl]propanoate (10 g) in tetrahydro-furan (100 mL) was added slowly over ca 12 minutes and the mixture then stirred at −70° C. for 1 hr prior to the addition of N-chlorosuccinimide (3.75 g). The mixture was allowed to warm to room temperature and stirred for an additional 25 hrs. The mixture was concentrated in vacuo and the residue diluted with water (500 mL) and extracted with ethyl acetate (3×400 mL). The combined organic layers were washed with brine (1 L), dried (MgSO$_4$) and evaporated. The resulting gum was chromatographed on silica gel with 2% ethyl acetate in dichloromethane as eluent to afford the title compound, mp 56°–7° C. (ether-hexane).

$^1$H NMR δ (CDCl$_3$) 3.07 (1H,dd); 3.28 (1H,dd); 3.34 (3H,s); 3.72 (3H,s); 3.94 (2H,t); 4.24 (2H,t); 4.38 (1H,t); 6.82 (2H,d); and 6.90–7.40 (6H,complex).

Method B

A solution of diethyl azodicarboxylate (0.75 mL) in dry tetrahydrofuran (2.5 mL) was added dropwise to a stirred, ice-cooled mixture of methyl 2-chloro-3-(4-hydroxyphenyl)-propanoate (1.00 g), 2-[N-(2-benzoxazolyl)-N-methylamino]-ethanol (0.89 g) and triphenylphosphine (1.22 g) in tetrahydrofuran (50 mL) under a nitrogen atmosphere. The resulting mixture was stirred at 0° C. for 45 minutes, then at room temperature for a further 24 hrs. The mixture was concentrated in vacuo and the residue suspended in dry diethyl ether (100 mL) and filtered. The ether solution was evaporated and the resulting gum chromatographed on silica gel with 1% methanol in dichloromethane as eluent. The impure product thus obtained was dissolved in dichloromethane (100 mL), washed sequentially with saturated potassium carbonate solution (100 mL), water (3×100 mL) and brine (100 mL), dried (MgSO$_4$) and evaporated. The residue was chromatographed on silica gel using a gradient of 2.5% ethyl acetate to 5% ethyl acetate in dichloromethane as eluent to afford the title compound, identical to that produced by Method A.

EXAMPLE 2

Methyl 3-[4-[2-[N-(2-benzoxazolyl-N-methylamino]ethoxy]phenyl]-2-bromopropanoate

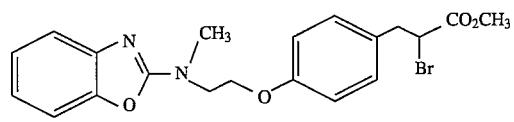

A solution of lithium diisopropylamide (2M, 11.25 mL) was added to a solution of chlorotrimethylsilane (2.85 mL) in dry tetrahydrofuran (70 mL) at −70° C. under a nitrogen atmosphere. A solution of methyl 3-[4-[2-[N-(2-benzoxazolyl)-N-methylamino]ethoxy]phenyl]propanoate (7.29 g) in tetrahydrofuran (55 mL) was added slowly over ca 5 minutes and the mixture stirred for 1 hr at −70° C. prior to the addition of N-bromosuccinimide (3.80 g). The mixture was allowed to warm to room temperature and stirred for a further 16 hrs, then concentrated in vacuo. The residue was diluted with water (500 mL) and extracted with dichloromethane (3×400 mL). The combined organic solutions were washed with water (3×500 mL) and brine (500 mL) dried (MgSO₄) and evaporated. The resulting gum was chromatographed on silica gel with dichloromethane as eluent to afford the title compound, a viscous gum.

$^1$H NMR δ (CDCl₃) 3.06 (1H, dd); 3.24 (3H, s); 3.28 (1H, dd); 3.60 (3H, s); 3.85 (2H, t); 4.13 (2H, t); 4.22 (1H, dd); 6.71 (2H, d); and 6.80–7.30 (6H, complex).

EXAMPLE 3

Methyl 3-[4-[2-[N-(2-benzoxazolyl)-N-methylamino]ethoxy] phenyl]-2-iodopropanoate

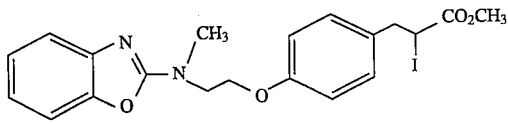

The title compound, a gum, was prepared from methyl 3-[4-[2-[N-(2-benzoxazolyl)-N-methylamino]ethoxy]phenyl]propanoate by a procedure similar to that described in Example 1 (Method A), and using N-iodosuccinimide as iodinating agent.

$^1$H NMR δ (CDCl₃) 3.17 (1H,dd); 3.34 (3H,s); 3.38 (1H,dd); 3.68 (3H,s); 3.94 (2H,t); 4.24 (2H,t); 4.43 (1H,dd); 6.81 (2H,d); and 6.90–7.40 (6H,complex).

EXAMPLE 4

Methyl 3-[4-[2-[N-methyl-N-(2-pyridyl)amino]ethoxy] phenyl]-2-chloropropanoate

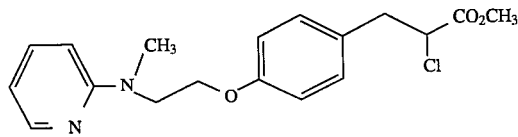

The title compound, a gum, was prepared from methyl 3-[4-[2-[N-methyl-N-(2-pyridyl)amino]ethoxy]phenyl]propanoate by a procedure similar to that described in Example 1 (Method A).

$^1$H NMR δ (CDCl₃) 3.09 (1H,dd); 3.13 (3H,s); 3.28 (1H,dd); 3.71 (3H,s); 3.96 (2H,t); 4.15 (2H,t); 4.38 (1H, t); 6.50 (2H,complex); 6.83 (2H,d); 7.08 (2H,d); 7.44 (1 H,complex); and 8.15 (1H,complex).

EXAMPLE 5

Methyl 4-[4-[2-[N-(2-benzoxazolyl)-N-methylamino]ethoxy] phenyl]-2-chlorobutanoate

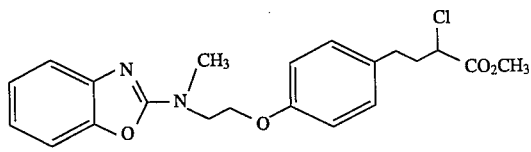

The title compound, a gum, was prepared from methyl 4-[4-[2-[N-(2-benzoxazolyl)-N-methylamino]ethoxy]phenyl]butanoate by a procedure similar to that described for Example 1 (Method A).

$^1$H NMR δ (CDCl₃) 2.25 (2H,complex); 2.70 (2H,complex); 3.34 (3H,s): 3.74 (3H,s); 3.93 (2H,t); 4.20 (3H, complex); 6.82 (2H,d); and 6.90–7.40 (6H,complex).

EXAMPLE 6

3-[4-[2-[N-(2-Benzoxazolyl)-N-methylamino]ethoxy] phenyl]-2-chloropropanoic Acid

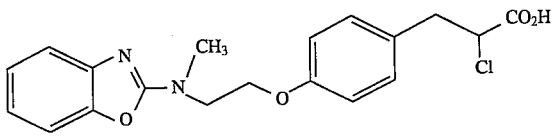

A mixture of methyl 3-[4-[2-[N-(2-benzoxazolyl)-N-methylamino]ethoxy]phenyl]-2-chloropropanoate (0.94 g), 10% aqueous sodium hydroxide solution (5 mL) and methanol (15 mL) was stirred at room temperature for 1.75 hrs. The mixture was then diluted with water (400 mL) and washed with dichloromethane (300 mL). The aqueous layer was acidified to pH 2 with concentrated hydrochloric acid and extracted with ethyl acetate (2×250 mL). The combined ethyl acetate extracts were washed with water (500 mL), brine (500 mL), dried (MgSO₄) and evaporated. The residue was crystallised from dichloromethane-hexane to afford the title compound, mp 142°–3° C.

$^1$H NMR δ (DMSO-d₆) 2.99 (1H,dd); 3.22 (4H,complex); 3.88 (2H,t); 4.22 (2H,t); 4.58 (1H,t); 6.75–7.40 (8H,complex); and 13.25 (1H, broad, exchanges with D₂O).

EXAMPLE 7

3-[4-[2-[N-(2-Benzoxazolyl)-N-methylamino] ethoxy]phenyl]-2-chloropropanamide

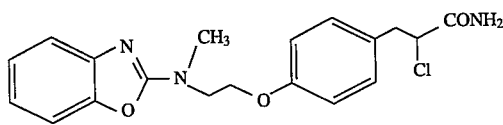

A mixture of methyl 3-[4-[2-[N-(2-benzoxazolyl)-N-methylamino]ethoxy]phenyl]-2-chloropropanoate (2.36 g), tetrahydrofuran (40 mL), methanol (40 mL) and aqueous ammonia solution (specific gravity 0.88; 40 mL) was stirred at room temperature for 2.5 hrs. The organic solvents were evaporated in vacuo and the residue was diluted with water (1 L) and extracted with dichloromethane (3×400 mL). The combined dichloromethane layers were washed with dilute hydrochloric acid solution (2M; 400 mL), water (1 L), brine (1 L), dried (MgSO₄) and evaporated. The residue was chromatographed on silica gel with 1.5% methanol in dichloromethane as eluent to afford the title compound, mp 149°–151° C. after recrystallisation from dichloromethane-hexane.

$^1$H NMR δ (DMSO-d₆) 2.92 (1H,dd); 3.17 (1H,dd); 3.22 (3H,s); 3.88 (2H,t); 4.22 (2H,t); 4.44 (1H,t); 6.80–7.40 (9H,complex; reduces to 8H on shaking with D₂O); and 7.60 (1H,s, exchanges with D₂O).

EXAMPLE 8

3-[4-[2-[N-(2-Benzoxazolyl)-N-methylamino]
ethoxy]phenyl]-2-chloro-N,N-dimethylpropanamide

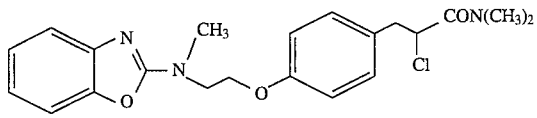

The title compound, a gum, was prepared from 3-[4-[2-[N-(2-benzoxazolyl)-N-methylamino]ethoxy]phenyl]-N,N-dimethylpropanamide by a procedure similar to that described in Example 1 (Method A).

$^1$H NMR δ (CDCl$_3$) 2.93 (3H,s); 2.94 (3H,s); 3.08 (1H, dd); 3.34 (3H,s); 3.40 (1H,dd); 3.93 (2H,t); 4.24 (2H,t); 4.55 (1H,dd); 6.80 (2H,d); and 6.95–7.40 (6H,complex).

EXAMPLE 9

Ethyl 3-[4-[2-[N-(2-benzoxazolyl)-
N-methylamino]ethoxy]phenyl]- 2-fluoropropanoate

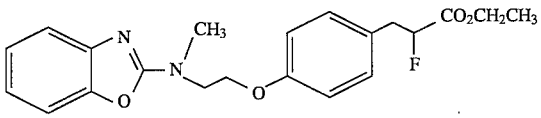

A solution of ethyl (E)-3-[4-[2-[N-(2-benzoxazolyl)-N-methylamino]ethoxy]phenyl]-2-fluoropropenoate (3.79 g) in ethanol (80 mL) was hydrogenated over 10% Palladium-charcoal (0.74 g) at room temperature and pressure for 3 hrs. The mixture was filtered, concentrated in vacuo and the residue chromatographed twice on silica gel, firstly with 10% ethyl acetate in dichloromethane and then with 25% ethyl acetate in hexane as eluents to afford a gum. Crystallisation from ethyl acetate-hexane afforded the title compound, mp 65°–7° C.

$^1$NMR δ (CDCl$_3$) 1.24 (3H,t); 3.10 (2H,complex); 3.33 (3H,s); 3.92 (2H,t); 4.20 (2H,q); 4.23 (2H,t); 5.02 (1H, ddd, $^2J_{H,F}$=48.9 Hz); 6.82 (2H,d); 6.99 (1H,td); 7.10–7.20 (3H, complex); 7.24 (1H,d); and 7.36 (1H,d).

$^{13}$C NMR δ (CDCl$_3$) 14.1 (s); 37.3 (s); 37.8 (d, $^2J_{C,F}$=21.0 Hz); 50.1 (s); 61.5 (s); 66.2 (s); 89.4 (d, $^1J_{C,F}$=186.9 Hz); 108.7 (s); 114.6(s); 116.1 (s); 120.4(s); 124.0(s); 127.6(s); 130.5 (s); 143.5 (s); 149.0 (s); 157.7 (s); 162.5 (s); and 169.2 (d, $^2J_{C,F}$=23.6 Hz).

EXAMPLE 10

3-[4-[2-[N-(2-Benzoxazolyl)-N-methylamino]
ethoxy]phenyl]- 2-fluoropropanoic Acid

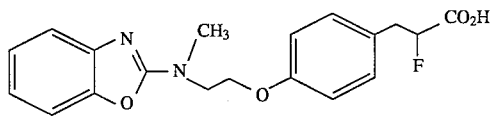

The title compound, mp 146°–8° C. (dichloromethane) was prepared from ethyl 3-[4-[2-[N-(2-benzoxazolyl)-N-methylamino]ethoxy]phenyl]-2-fluoropropanoate by a procedure similar to that described for Example 6.

$^1$H NMR δ (DMSO-$_6$) 2.85–3.15 (2H,complex); 3.22 (3H,s); 3.89 (2H,t); 4.23 (2H,t); 5.15 (1H, ddd, $^2J_{H,F}$=48.7 Hz); 6.87 (2H,d), 6.90–7.40 (6H,complex); and 13.25 (1H, broad, exchanges with D$_2$O).

EXAMPLE 11

3-[4-[2-[N-(2-Benzoxazolyl)-N-methylamino]
ethoxy]phenyl]-2-fluoropropanamide

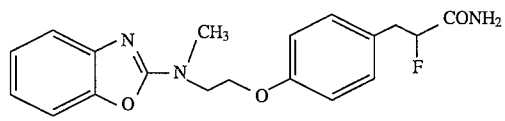

The title compound, mp 168°–70° C. (dichloromethane-hexane) was prepared from ethyl 3-[4-[2-[N-(2-benzoxazolyl)-N-methylamino]ethoxy]phenyl]-2-fluoropropanoate by a procedure similar to that described in Example 7.

$^1$H NMR δ (CDCl$_3$) 3.10 (1H, ddd, $^3J_{H,F}$=29.9 Hz) 3.20 (1H, ddd, $^3J_{H,F}$=26.9 Hz); 3.34 (3H,s); 3.94 (2H,t); 4.25 (2H,t); 5.04 (1H, ddd, $^2J_{H,F}$=49.5 Hz); 5.46 (1H, broad, exchanges with D$_2$O); 6.10 (1H, broad, exchanges with D$_2$O); 6.83 (2H,d); and 6.95–7.40 (6H,complex).

EXAMPLE 12

Ethyl (E)-3-[4-[2-[N-(2-benzoxazolyl)-
N-methylamino]ethoxy]-phenyl]-
2-fluoropropenoate

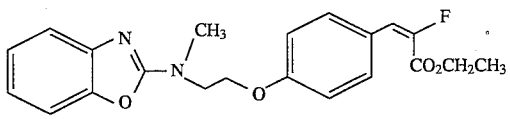

n-Butyl lithium (2.5M solution in hexane; 9.9 mL,) was added dropwise to a cooled (−78° C.) solution of triethyl 2-fluorophosphonoacetate (J. Org. Chem., 1990, 55, 4639) (6.0 g) in dry tetrahydrofuran (30 mL) under a nitrogen atmosphere. The mixture was stirred at −78° C. for 1 hr, then transferred via a syringe into a cold (−78° C.) solution of 4-[2-[N-(2-benzoxazolyl)-N-methylamino]ethoxy]benzaldehyde (Eur. Pat. Appl., Publication No. 0306228) (7.3 g) in dry tetrahydrofuran (30 mL) under a nitrogen atmosphere. The mixture was allowed to warm to room temperature, with stirring, over 18 hrs, then quenched by the addition of concentrated hydrochloric acid (30 mL) and concentrated in vacuo. The residue was suspended in water (500 mL) and extracted with ethyl acetate (3×200 mL). The combined ethyl acetate solutions were washed with water (500 mL) and brine (500 mL), dried (MgSO$_4$) and evaporated to afford an oil. This was chromatographed twice on silica gel, firstly in 6% ethyl acetate in dichloromethane and then in 50% ethyl acetate in hexane as eluents to afford the title compound, a gum, which was used in subsequent reactions without further purification.

$^1$H NMR δ (CDCl$_3$) 1.27 (3H,t); 3.33 (3H,s); 3.94 (2H,t); 4.26 (2H,t); 4.27 (2H,t); 6.81 (1H,d, $^3J_{H,F}$=23.5 Hz) 6.85 (2H,d); 7.00 (1H,t); 7.15 (1H, t); 7.25 (1H,d); 7.36 (1H,d); and 7.47 (2H,d).

$^{13}$C NMR δ (CDCl$_3$) 14.0 (s); 37.4 (s); 50.1 (s); 61.5 (s); 66.2 (s); 108.8 (s); 114.1 (s); 116.1 (s); 120.6 (s); 121.7 (d, $^2J_{C,F}$26.9 Hz); 123.6 (d, $^3J_{C,F}$=9.5 Hz); 124.1 (s); 131.7 (s); 143.1 (s); 146.0 (d, $^1J_{C,F}$=252.8 Hz); 148.9 (s); 158.9 (s);

160.7 (d, $^2J_{C,F}$=35.4 Hz); and 162.3 (s). This data is consistent with E-double bond geometry (cf *J. Org. Chem.*, 1990, 55, 4639).

EXAMPLE 13

Methyl 3-[4-[2-[N-(2-benzoxazolyl)-N-methylamino]ethoxy]phenyl]-2-(methylthio)propanoate

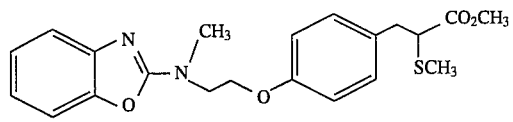

Method A

Sodium hydride (60% dispersion in oil; 0.78 g) was added portionwise to a stirred, ice-cooled solution of methyl 3-(4-hydroxyphenyl)-2-(methylthio)propanoate (4.00 g) in dry N,N-dimethylformamide (100 mL) under a nitrogen atmosphere. The mixture was stirred for 30 minutes at room temperature prior to the addition of a solution of 2-[N-(2-benzoxazolyl)-N-methylamino]ethanol methanesulphonyl ester (*Eur. Patent Appl., Publication No:* 0306228) (4.21 g) in N,N-dimethylformamide (200 mL). The mixture was heated at 80° C. for 19 hrs, cooled and diluted with water (1 L), then extracted with ethyl acetate (4×500 mL). The combined organic solutions were washed with water (4×1 L) and brine (1 L), dried (MgSO$_4$) and concentrated in vacuo. The residue was chromatographed on silica gel using dichloromethane as eluent to afford the title compound, mp 70°–71° C. (ethyl acetate-hexane).

$^1$H NMR δ (CDCl$_3$) 2.15 (3H, s); 2.89 (1H, dd); 3.13 (1H, dd); 3.34 (3H, s); 3.40 (1H,dd); 3.66 (3H,s); 3.93 (2H, t); 4.23 (2H, t); 6.80 (2H, d); and 6.95–7.40 (6H, complex).

Method B

A mixture of methyl 3-[4-[2-[N-2-benzoxazolyl]-N-methylamino]ethoxy]phenyl]-2-bromopropanoate (0.80 g) and sodium thiomethoxide (0.26 g) in tetrahydrofuran (20 mL) and methanol (20 mL) was heated at reflux for 3 hrs, cooled and concentrated. The residue was diluted with water (100 mL) and extracted with ethyl acetate (3×100 mL). The combined organic solutions were washed with water (500 mL) and brine (500 mL) dried (MgSO$_4$) and evaporated. The resulting gum was chromatographed on silica gel using a gradient of 0.5% methanol to 2% methanol in dichloromethane as eluent to afford the title compound, identical to that produced by Method A.

EXAMPLE 14

3-[4-[2-[N-(2-Benzoxazolyl)-N-methylamino]ethoxy]phenyl]-2(methylthio)propanoic Acid

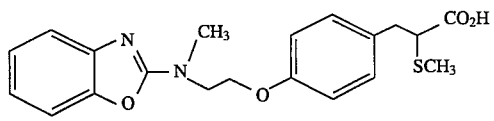

A mixture of methyl 3-[4-[2-[N-(2-benzoxazolyl)-N-methylamino]ethoxy]phenyl]-2-(methylthio)propanoate (1.01 g), 10% aqueous sodium hydroxide solution (10 mL) and methanol (20 mL) was heated at reflux for 1 hour. The mixture was diluted with water (300 mL) and washed with dichloromethane (3×200 mL). The aqueous layer was acidified to pH2 with concentrated hydrochloric acid, extracted with ethyl acetate (3×200 mL) and the extracts washed with brine (2×200 mL), dried (MgSO$_4$) and evaporated. The residue was chromatographed on silica gel with 2% methanol in dichloromethane as eluent to afford the title compound, mp 140°–1° C. (ethyl acetate-hexane).

$^1$H NMR δ (DMSO-d$_6$) 2.10 (3H, s); 2.77 (1H, dd); 2.99 (1H, dd); 3.23 (3H, s); 3.40 (1H, dd); 3.87 (2H, t); 4.21 (2H, t); 6.83 (2H, d); 6.90–7.40 (6H, complex); and 12.48 (1H, broad, exchanges with D$_2$O).

EXAMPLE 15

3-[4-[2-[N-(2-Benzoxazolyl)-N-methylamino]ethoxy]phenyl]-2-(methylthio)-propanamide

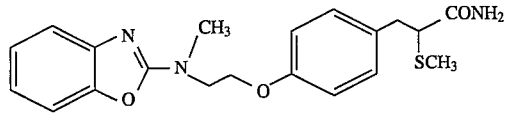

Method A

The title compound, mp 121°–2° C. (ethyl acetate-hexane) was prepared from 3-(4-hydroxyphenyl)-2-(methylthio)propanamide by a procedure similar to that described in Example 13 (Method A).

$^1$H NMR δ (DMSO-d$_6$) 2.05 (3H, s); 2.70 (1H, dd); 3.00 (1H,dd); 3.22 (3H, s); 3.31 (1H, dd); 3.87 (2H,t); 4.21 (2H, t); 6.83 (2H, d); 6.88 (1H, s, exchanges with D$_2$O); and 6.95–7.45 (7H, complex, reduced to 6H on shaking with D$_2$O).

Method B

The title compound, identical with that produced by Method A, was prepared from methyl 3-[4-[2-[N-(2-benzoxazolyl)-N-methylamino]ethoxy]phenyl]-2-(methylthio)propanoate and aqueous ammonia solution by a procedure similar to that described in Procedure 10.

EXAMPLE 16

3-[4-[2-[N-(2-Benzoxazolyl)-N-methylamino]ethoxy]phenyl]-2-mercaptopropanoic Acid

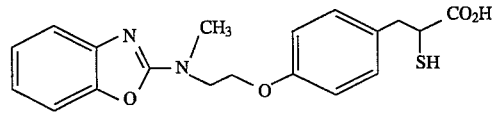

A solution of 5-[4-[2-[N-(2-benzoxazolyl)-N-methylamino]ethoxy]benzyl]-2,4-thiazolidinedione (*Eur. Patent Appl., Publication No.* 0306228) (1.0 g) in 10% aqueous sodium hydroxide solution (25 mL) was heated at reflux under a nitrogen atmosphere for 1.75 hrs. The mixture was cooled, acidified to pH3 with concentrated hydrochloric acid and extracted with ethyl acetate (300 mL). The organic solution was washed with brine (100 mL), dried (MgSO$_4$) and evaporated. The residue was redissolved in boiling ethyl acetate, filtered and allowed to cool and crystallise to afford the title compound, mp 154°–6° C.

$^1$H NMR δ (DMSO-d$_6$) 2.81 (1H, dd); 3.03 (1H, dd); 3.22 (3H, s); 3.31 (1H, broad, exchanges with D$_2$O); 3.53 (1H, dd); 3.87 (2H, t); 4.22 (2H, t); 6.84 (2H, d); 6.95–7.40 (6H, complex); and 12.60 (1H, broad, exchanges with D$_2$O).

EXAMPLE 17

Methyl 2-(acetylthio)-3-[4-[2-[N-(2-benzoxazolyl)-N-methylamino]ethoxy]phenyl]propanoate

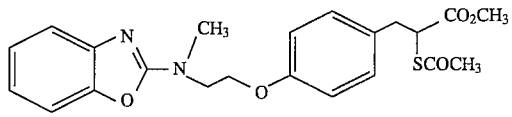

A mixture of methyl 3-[4-[2-[N-(2-benzoxazolyl)-N-methylamino]ethoxy]phenyl]-2-bromopropanoate (1.25 g), potassium thioacetate (0.5 g) and dry N,N-dimethylformamide (15 mL) was heated at 80° C. for 18 hours under a nitrogen atmosphere. The mixture was diluted with water (1 L) and extracted with ethyl acetate (3×250 mL). The combined ethyl acetate solutions were washed with water (3×250 mL) and brine (500 mL), dried (MgSO$_4$) and evaporated. The residue was chromatographed on silica gel with 40% ethyl acetate in hexane as eluent to afford the title compound, a gum.

$^1$H NMR δ (CDCl$_3$) 2.31 (3H, s); 2.94 (1H, dd); 3.16 (1H, dd); 3.35 (3H, s); 3.65 (3H, s); 3.94 (2H,t); 4.24 (2H, t); 4.38 (1H, t); 6.79 (2H, d); and 6.95–7.40 (6H, complex).

EXAMPLE 18

3-[4-[2-[N-(2-Benzoxazolyl)-N-methylamino]ethoxy]phenyl]-2-(2-aminoethylthio)propanoic Acid

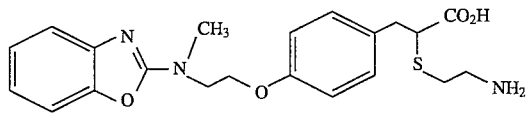

A solution of 2-[4-[2-[N-(2-benzoxazolyl)-N-methylamino]ethoxy]phenyl]perhydro-1,4-thiazin-3-one (0.75 g) in 10% aqueous sodium hydroxide solution (2.8 mL) was heated at reflux for 1 hr under a nitrogen atmosphere. The mixture was cooled and acidified to pH 6.5 with concentrated hydrochloric acid. The resulting precipitate was washed with water (60 mL) and ethyl acetate (70 mL) and dried in vacuo at 70° C. to afford the title compound, mp 200°–201° C.

$^1$H NMR δ (DMSO-d$_6$+D$_2$O) 2.57–2.67 (2H, complex); 2.78 (1H, complex); 2.90–3.02 (2H, complex); 3.07 (1H, dd); 3.22 (3H, s); 3.24 (1H, t); 3.88 (2H, t); 4.21 (2H, t); 6.80 (2H, d); 7.01 (1H,dt); 7.10–7.17 (3H, complex); 7.27 (1H, dd); and 7.37 (1H, d).

EXAMPLE 19

Methyl 3-[4-[2-[N-(2-benzoxazolyl)-N-methylamino]ethoxy]phenyl]-2-(phenylthio)propanoate

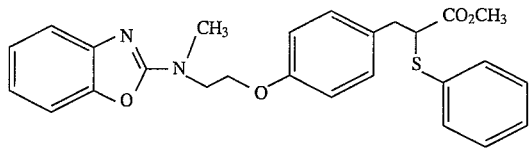

Thiophenol (0.92 mL) was added slowly to an ice-cooled, stirred suspension of sodium hydride (60% dispersion in oil, 0.38 g) in dry N,N-dimethylformamide (60 mL). The mixture was allowed to warm to room temperature over 30 minutes prior to the addition of a solution of methyl 3-[4-[2-[N-(2-benzoxazolyl)-N-methylamino]ethoxy]phenyl]-2-bromopropanoate (3.85 g) in N,N-dimethylformamide (40 mL) and the mixture was then heated at 80° C. for 72 hrs, cooled and diluted with water (1 L). The mixture was extracted with ethyl acetate (3×250 mL) and the combined organic solutions washed with water (3×1 L) and brine (1 L), dried (MgSO$_4$) and evaporated. The residue was chromatographed on silica gel using a gradient of 1% methanol to 2% methanol in dichloromethane as eluent to afford the title compound, mp 78°–9° C. (dichloromethane-hexane).

$^1$H NMR δ (CDCl$_3$) 2.99 (1H, dd); 3.11 (1H, dd); 3.34 (3H, s); 3.56 (3H, s); 3.84 (1H, dd); 3.92 (2H,t); 4.22 (2H, t); 6.78 (2H, d); and 6.95–7.50 (11H, complex).

EXAMPLE 20

Methyl 2-(benzenesulphonyl)-3-[4-[2-[N-(2-benzoxazolyl)-N-methylamino]ethoxy]phenyl]propanoate

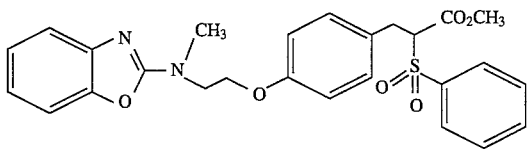

Method A

A mixture of methyl 3-[4-[2-[N-(2-benzoxazolyl)-N-methylamino]ethoxy]phenyl]-2-(phenylthio)propanoate (1.41 g) and monoperoxyphthalic acid magnesium salt hexahydrate (80% tech., 3.76 g) in methanol (40 mL) was heated at reflux for 48 hrs, then cooled and concentrated in vacuo. The residue was diluted with water (100 mL), extracted with ethyl acetate (3×100 mL) and the combined ethyl acetate solutions washed with water (2×200 mL), brine (100 mL), dried (MgSO$_4$) and evaporated. The residue was chromatographed on silica gel with 1% methanol in dichloromethane as eluent to afford the title compound, a viscous gum, which was used without further purification.

H NMR δ (CDCl$_3$) 3.13 (1H, dd); 3.31 (1H, dd); 3.32 (3H, s); 3.51 (3H, s); 3.92 (2H, t); 4.18 (1H,dd); 4.20 (2H, t); 6.76 (2H, d); and 6.90–7.90 (11H, complex).

Method B

The title compound was also prepared from methyl 2-(benzenesulphonyl)-3-(4-hydroxyphenyl)propanoate by a procedure similar to that described in Example 13 (Method A), and was identical to that prepared by Method A above.

EXAMPLE 21

2-(Benzenesulphonyl)-3-[4-[2-[N-(2-benzoxazolyl)-N-methylamino]ethoxy]phenyl]propanoic Acid

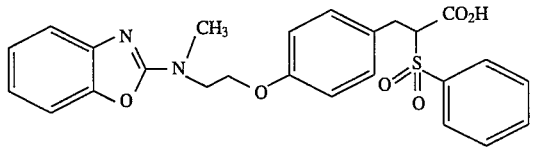

A mixture of methyl 2-(benzenesulphonyl)-3-[4-[2-[N-(2-benzoxazolyl)-N-methylamino]ethoxy]phenylpropanoate (0.94 g), 10% aqueous sodium hydroxide solution (5 mL) and methanol (15 mL) was stirred at room temperature for 1 hr. Water (400 mL) was added and the mixture extracted with dichloromethane (2×200 mL). The aqueous layer was acidified to pH2 with concentrated hydrochloric acid and then extracted with ethyl acetate (3×200 mL). the combined ethyl acetate layers were washed with brine (200 mL), dried (MgSO$_4$) and evaporated. The resulting solid was recrystallised from ethyl acetate to afford the title compound, mp 193°–6° C.

$^1$H NMR δ (DMSO-d$_6$) 3.00 (1H, dd); 3.15 (1H, dd); 3.20 (3H, s); 3.86 (2H, t); 4.20 (2H, t); 4.45 (1H, dd); 6.75–8.00 (13H, complex); and 13.20 (1H, broad, exchanges with D$_2$O).

EXAMPLE 22

3-[4-[2-[N-(2-Benzoxazolyl)-N-methylamino]ethoxy]phenyl]-2-(phenylthio)propanoic Acid

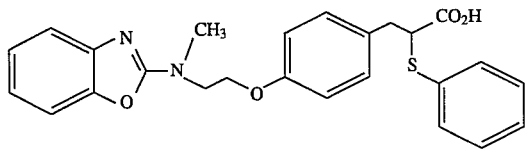

The title compound, mp 144°–7° C. (dichloromethane-hexane), was prepared from methyl 3-[4-[2-[N-(2-benzoxazolyl)-N-methylamino]ethoxy]phenyl]-2-(phenylthio)propanoate by a procedure similar to that described for Example 21.

$^1$H NMR δ (DMSO-d$_6$) 3.00 (1H,dd); 3.15 (1H,dd); 3.20 (3H,s); 3.86 (2H,t); 4.19 (2H,t); 4.46 (1H,dd); 6.81 (2H,d); 6.90–7.40 (6H,complex); 7.60–8.00 (5H,complex); and 13.25 (1H, broad, exchanges with D$_2$O).

EXAMPLE 23

Methyl 3-[4-[2-[N-(2-benzoxazolyl)-N-methylamino]ethoxy]phenyl]-2-(4-methylphenylthio)propanoate

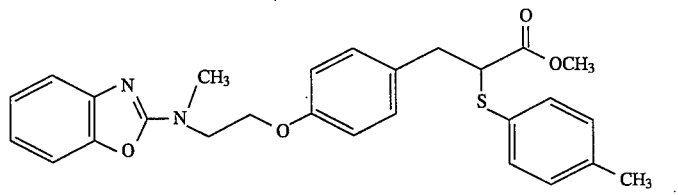

p-Thiocresol (0.43 g) was added slowly to an ice-cooled, stirred suspension of sodium hydride (60% dispersion in oil, 0.14 g) in dry N, N-dimethylformamide (23 mL,) under N$_2$. The mixture was allowed to warm to room temperature over 30 minutes prior to the addition of a solution of methyl 3-[4-[2-[N-(2-benzoxazolyl)-N-methylamino]ethoxy]phenyl]-2-chloropropanoate (1.31 g) in dry N,N-dimethylformamide (16 mL) and the mixture was then left stirring at room temperature for a further 12 hrs. The reaction mixture was diluted with water (375 mL) before extracting with ethyl acetate (3×100 mL). The combined ethyl acetate layers were washed with water (3×100 mL), dried (MgSO$_4$) and evaporated. The residue was chromatographed on silica gel using 60% hexane in ethyl acetate as eluent to afford the title compound which solidified on standing, mp 88.6°–90.1° C.

$^1$H NMR δ (CDCl$_3$) 2.32 (3H,s); 2.92–3.31 (2H,m); 3.34 (3H,s); 3.57 (3H,s); 3.76 (1H,dd); 3.93 (2H,t); 4.22 (2H,t); 6.76–7.37 (12H,complex).

EXAMPLE 24

3-[4-[2- [N-(2-Benzoxazolyl)-N-methylamino]ethoxy]phenyl]-2-(4-methylphenylthio)propanoic Acid

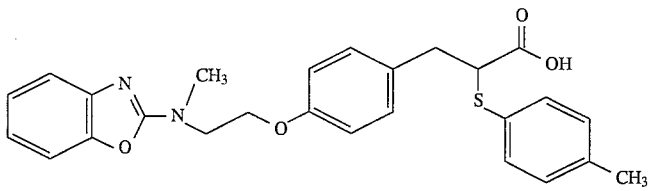

Methyl 3-[4-[2-[N-(2-benzoxazolyl)-N-methylamino]ethoxy]phenyl]-2-(4-methylphenylthio)propanote (1.21 g) was dissolved in a mixture of methanol (13.7 mL) and tetrahydrofuran (5.5 mL) prior to the addition of a 10% solution of sodium hydroxide (2.2 mL). The reaction was left stirring at room temperature for 18 hrs before being diluted with water (100 mL). The aqueous solution was acidified to pH 2 using hydrochloric acid (2M) then extracted with ethyl acetate (3×50 mL). The combined ethyl acetate layers were washed with water (4×100 mL), dried (MgSO$_4$) and evaporated. The product was recrystallised from ethyl acetate/hexane to afford the title compound, mp 136.6°–137.1° C.

$^1$H NMR δ (CDCl$_3$) 2.32 (3H,s); 3.00–3.06 (2H,complex); 3.25 (3H,s); 3.68–3.94 (5H,complex); 6.67–7.47 (12H,complex); the exchangeable proton was not observed.

EXAMPLE 25

Methyl 3-[4-[2-[N-(2-benzoxazolyl)-N-methylamino]ethoxy]phenyl]-2-(4-methoxyphenylthio)propanoate

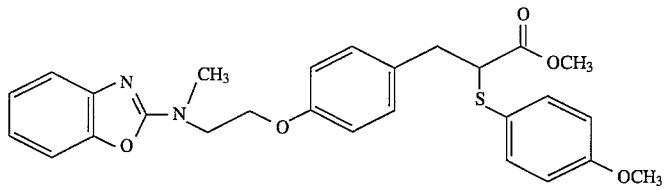

The title compound was prepared as a gum from methyl 3-[4-[2-[N-(2-benzoxazolyl)-N-methylamino]ethoxy]phenyl]-2-chloropropanoate and 4-methoxythiophenol by a procedure similar to that described in Example 23.

$^1$H NMR δ (CDCl$_3$) 2.91–3.10 (2H,m); 3.34 (3H,s); 3.56 (3H,s); 3.69 (1H,dd); 3.79 (3H,s); 3.93 (2H,t); 4.23 (2H,t); 6.77–7.41 (12H,complex).

EXAMPLE 26

3-[4-[2-[N-(2-Benzoxazolyl)-N-methylamino]ethoxy]phenyl]-2-(4-methoxyphenylthio)propano Acid

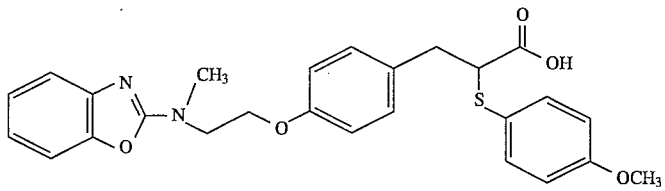

The title compound, mp 137.1°–140.1° C. (toluene) was prepared from methyl 3-[4-[2-[N-(2-benzoxazolyl)-N-methylaminolethoxy]phenyl]-2-(4-methoxyphenylthio)propanoate by a procedure similar to that described in Example 24.

$^1$H NMR δ (CDCl$_3$) 3.03 (2H,complex); 3.25 (3H,s); 3.67–3.90 (8H,complex); 6.66–7.52 (12H,complex); 9.00 (1H,broad,exchanges with D$_2$O).

EXAMPLE 27

Methyl 3-[4-[2-[N-(2-benzoxazolyl)-N-methylamino]ethoxy]phenyl]-2-(4-chlorophenylthio)propanoate

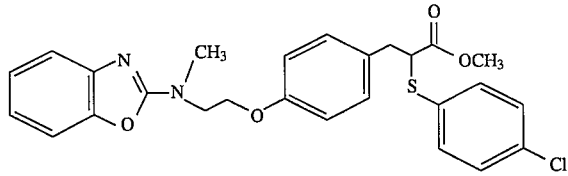

The title compound was prepared as a gum from methyl 3-[4-[2-[N-(2-benzoxazolyl)-N-methylamino]ethoxy]phenyl]-2-chloropropanoate and 4-chlorothiophenol by a procedure similar to that described in Example 23.

$^1$H NMR δ (CDCl$_3$) 2.94–3.15 (2H,m); 3.34 (3H,s); 3.58 (3H,s); 3.86 (1H,dd); 3.93 (2H,t); 4.23 (2H,t); 6.78–7.37 (12H,complex).

EXAMPLE 28

3-[4-[2-[N-(2-Benzoxazolyl)-N-methylamino]ethoxy]phenyl]-2-(4-chlorophenylthio)propanoic Acid

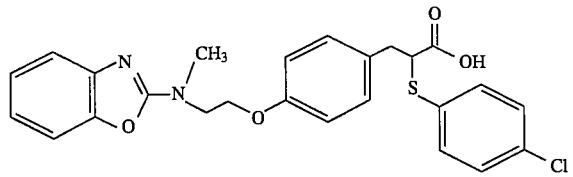

The title compound, mp 156.1°–157.4° C. (toluene), was prepared from methyl 3-[4-[2-[N-(2-benzoxazolyl)-N-methylamino)ethoxy]phenyl]-2-(4-chlorophenylthio)propanoate by a procedure similar to that described in Example 24.

$^1$H NMR δ (CDCl$_3$) 3.10 (2H,complex); 3.26 (3H,s); 3.64–3.94 (5H,complex); 6.67–7.48 (12H,complex); the exchangeable proton was not observed.

EXAMPLE 29

Methyl 3-[4-[2-[N-(2-benzoxazolyl)-N-methylamino]ethoxy]phenyl-2-(2-propylthio)propanoate

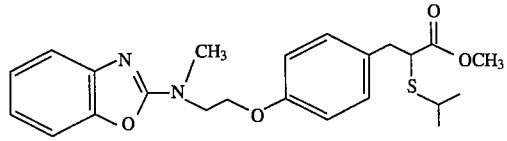

The title compound was prepared as a gum from methyl 3-[4-[2-[N-(2-benzoxazolyl)-N-methylamino]ethoxy]phenyl]-2-chloropropanoate and 2 to propanethiol by a procedure similar to that described in Example 23.

$^1$H NMR δ (CDCl$_3$) 1.26 (6H,m); 2.89–3.09 (3H,complex); 3.34 (3H,s); 3.51 (1H,dd); 3.65 (3H,s); 3.93 (2H,t); 4.23 (2H,t); 6.78–7.37 (8H,complex).

EXAMPLE 30

3-[4-[2-[N-(2-Benzoxazolyl)-N-methylamino]ethoxy]phenyl]-2-(2-propylthio)propanoic Acid

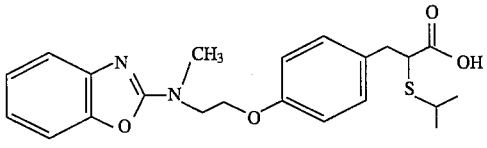

The title compound, mp 143.9°–144.8° C. (toluene), was prepared from methyl 3-[4-[2-[N-(2-benzoxazolyl)-N-methylamino]ethoxy]phenyl]-2-(2-propylthio)propanoate by a procedure similar to that describe in Example 24.

$^1$H NMR δ (CDCl$_3$) 1.25–1.33 (6H,m); 2.89 (1H,dd); 3.06–3.18 (2H,complex); 3.30 (3H,s); 3.59 (1H,dd); 3.78–4.06 (4H,complex); 6.72–7.36 (8H,complex); the exchangeable proton was not observed.

EXAMPLE 31

3-[4-[2-[N-Methyl-N-(2-pyridyl)amino]ethoxy] phenyl]-2-mercaptopropanoic Acid

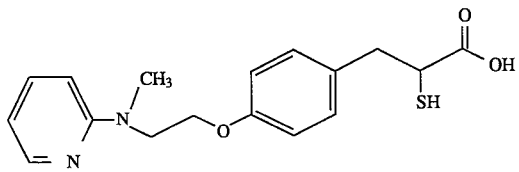

A solution of 5-[4-[2-[N-methyl-N-(2-pyridyl)amino]ethoxy]benzyl]-2,4-thiazolidinedione (Eur. Patent Appl., Publication No. 0306228) (3.4 g) in 10% aqueous sodium hydride solution (100 mL) was heated at reflux for 6 hrs. The mixture was cooled and acidified to pH 6 with dilute hydrochloric acid, then extracted with ethyl acetate (2×100 mL). The combined ethyl acetate layers were dried (MgSO$_4$) and evaporated. The residue was crystallised from methanol to afford the title compound, mp 110°–114° C.

$^1$H NMR δ (DMSO-d$_6$) 2.83 (1H,dd); 2.98–3.07 (5H, complex, reduces to 4H on exchange with D$_2$O); 3.54 (1H,dd); 3.88 (2H,t); 4.10 (2H,t); 6.58 (1H,dd); 6.67 (1H, complex); 6.84 (2H,d); 7.13 (2H,d); 7.51 (1H,complex); 8.06 (1H,dd); and 12.3–13.0 (1H,broad, exchanges with D$_2$O).

EXAMPLE 32

Methyl 3-[4-[2-[N-(2-benzoxazolyl)-N-methylamino]ethoxy]phenyl]-2-(2-pyridylthio)propanoate

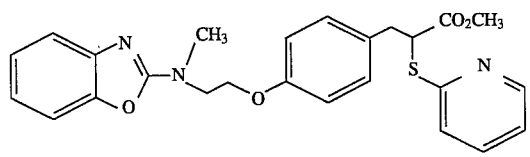

Sodium hydride (60% dispersion in oil; 0.21 g) was added to a stirred, ice-cooled solution of 2-mercaptopyridine (0.57 g) in dry N,N-dimethylformamide (25 mL) under nitrogen. The mixture was stirred at 0° C. for 1 hr prior to the addition of a solution of methyl 3-[4-[2-[N-(2-benzoxazolyl)-N-methylamino]ethoxylphenyl]-2-chloropropanoate (2.00 g) in N,N-dimethylformamide (50 mL). The resulting mixture was stirred at 0° C. for 30 minutes, then heated at 80° C. for 18 hrs before being allowed to stand at ambient temperature for 48 hrs.

The bulk of the solvent was evaporated and the residue suspended in water (1 L) and extracted with ethyl acetate (3×400 mL). The combined ethyl acetate layers were washed with water (3×1 L) and brine (1 L), dried (MgSO$_4$) and evaporated. The resulting gum was chromatographed on silica gel with a gradient of 2.5 to 10% ethyl acetate in dichloromethane as eluent. Subsequent further chromatography on silica gel with 1.5% methanol in dichloromethane as eluent afforded the title compound as a gum.

$^1$H NMR δ (CDCl$_3$) 3.12 (1H,dd); 3.23 (1H,dd); 3.33 (3H,s); 3.63 (3H,s); 3.92 (2H,t); 4.23 (2H,t); 4.81 (1H,t); 6.79 (2H,d); 7.00 (2H,complex); 7.10–7.20 (4H,complex); 7.25 (1H,d); 7.35 (1H,d); 7.45 (1H,dt); and 8.40 (1H,dd).

PROCEDURE 1

Methyl 3-[4-[2-[N-(2-benzoxazolyl)-N-methylamino]ethoxy]phenyl]propanoate

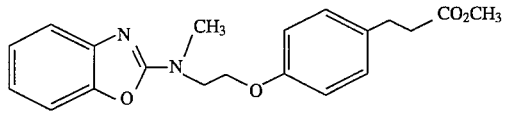

Sodium hydride (60% dispersion in oil, 2.51 g) was added portionwise to a stirred, ice cooled solution of methyl 3-(4-hydroxyphenyl)propanoate (10.25 g) in dry N,N-dimethylformamide (100 mL) under a nitrogen atmosphere. The mixture was stirred for 40 minutes at room temperature prior to the addition of a solution of 2-[N-(2-benzoxazolyl)-N-methylamino]ethanol methanesulphonyl ester (*Eur. Patent Appl., Publication No. 0306228*) (15.39 g) in N,N-dimethylformamide (150 mL). The mixture was heated at 80° C. for 23.5 hrs, cooled and concentrated in vacuo, then diluted with water (1 L) and extracted with ethyl acetate (3×400 mL). The combined organic extracts were washed with water (2×1 L) and brine (1 L), dried (MgSO$_4$) and evaporated. The residue was chromatographed on silica gel using 1.5% ethyl acetate in dichloromethane as eluent to afford the title compound, mp 51°–2° C.

$^1$H NMR δ (CDCl$_3$) 2.58 (2H,t); 2.88 (2H,t); 3.34 (3H,s); 3.65 (3H,s); 3.93 (2H,t); 4.23 (2H,t); 6.81 (2H,d); and 6.90–7.45 (6H,complex).

PROCEDURE 2

Methyl 2-chloro-3-(4-hydroxyphenyl)propanoate

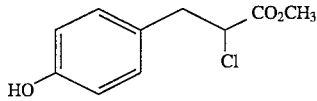

A solution of boron tribromide—dimethyl sulphide complex (9.4 g) in dichloromethane (100 mL) was added over 10 minutes to a stirred, ice cooled solution of methyl 3-(4-benzyloxyl)phenyl-2-chloropropanoate (6.08 g) (*International Patent Appl., Publication No. WO 9101337*) in dichloromethane (50 mL). The mixture was stirred at 0° C. for 30 minutes, heated at reflux for a further hour, then cooled and diluted with water (300 mL). The layers were separated and the aqueous layer extracted with dichloromethane (2×100 mL). The combined organic layers were washed with water (2×200 mL), dried (MgSO$_4$) and evaporated. The residue was chromatographed on silica gel with 1.5% methanol in dichloromethane as eluent to afford the title compound, mp 57°–9° C.

$^1$H NMR δ (CDCl$_3$) 3.11 (1H,dd); 3.28 (1H,dd); 3.73 (3H,s); 4.40 (1H,t); 5.31 (1H,s, exchanges with D$_2$O); 6.77 (2H,d); and 7.07 (2H,d).

PROCEDURE 3

Methyl E-3-[4-[2-[N-methyl-N-(2-pyridyl)amino]ethoxy]phenyl]prop-2-enoate

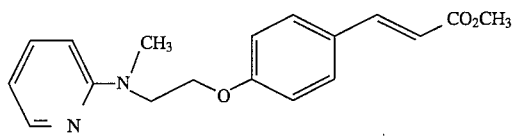

A solution of trimethyl phosphonoacetate (5.5 mL) in dry tetrahydrofuran (25 mL) was added slowly to a cooled (cardice-acetone bath) suspension of sodium hydride (60% dispersion in oil, 1.34 g) in tetrahydrofuran (100 mL) under a nitrogen atmosphere such that the temperature of the reaction mixture remained between 0° C. and 10° C. during the addition. The resultant slurry was then cooled in an ice bath and stirred for 10 minutes prior to the addition of a solution of 4-[2-[N-methyl-N-(2-pyridyl)amino]ethoxy]benzaldehyde (8.3 g) (*Eur. Patent. Appl., Publication No. 0306228*) in tetrahydrofuran (100 mL). The mixture was stirred at room temperature for 20 hrs, then quenched with brine (10 mL) and concentrated in vacuo. The residue was suspended in brine (500 mL) and extracted with dichloromethane (3×300 mL), and the combined organic layers were washed with water (1 L) and brine (1 L), dried (MgSO$_4$) and evaporated. The residue was chromatographed on silica gel with 1% methanol in dichloromethane as eluent to afford the title compound, mp 93°–5° C. (dichloromethane-hexane).

$^1$H NMR δ (CDCl$_3$) 3.15 (3H,s); 3.80 (3H,s); 4.00 (2H,t); 4.27 (2H,t); 6.35 (1H,d); 6.60 (2H,complex); 6.93 (2H,d); 7.10–7.80 (4H,complex); and 8.23 (1H,d).

PROCEDURE 4

Methyl 3-[4-[2-[N-methyl-N-(2-pyridyl)amino]ethoxy]phenyl]propanoate

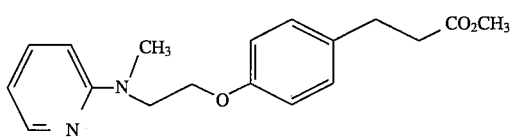

Methyl E-3-[4-[2-[N-methyl-N-(2-pyridyl)amino]ethoxy]phenyl]prop-2-enoate (7.00 g) was suspended in methanol (220 mL) and hydrogenated over platinum (IV) oxide catalyst (0.44 g total) for a total of 28 hrs. The mixture was filtered through filter aid and the solvent evaporated. The residue was chromatographed on silica gel with 1% methanol in dichloromethane as eluent to afford the title compound as a gum which was used without further purification.

¹H NMR δ (CDCl₃) 2.57 (2H,t); 2.87 (2H,t); 3.14 (3H,s); 3.65 (3H,s); 3.96 (2H,t); 4.14 (2H,t); 6.52 (2H,complex); 6.81 (2H,d); 7.07 (2H,d); 7.43 (1H,complex); and 8.14 (1H,ddd).

PROCEDURE 5

Methyl 4-[4-[2-[N-(2-benzoxazolyl)-N-methylamino]ethoxy]phenyl]butanoate

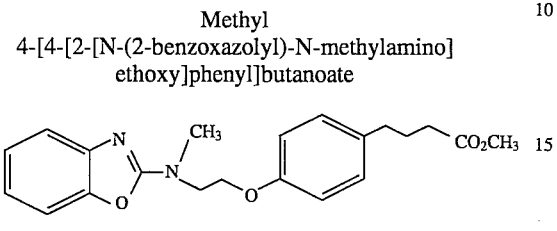

The title compound, an oil, was prepared from methyl 4-(4-hydroxyphenyl)butanoate by a procedure similar to that described for Procedure 1.

¹H NMR δ (CDCl₃) 2.00 (2H,complex); 2.32 (2H,t); 2.61 (2H,t); 3.35 (3H,s); 3.70 (3H,s); 3.95 (2H,t); 4.27 (2H,t); and 6.80–7.50 (8H,complex).

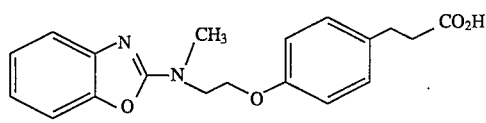

The title compound, mp 117°–9° C. (dichloromethane-hexane) was prepared from methyl 3-[4-[2-[N-(2-benzoxazolyl)-N-methylaminolethoxy]-phenyl]propanoate by a procedure similar to that described in Example 6.

¹H NMR δ (DMSO-d₆) 2.46 (2H,t); 2.74 (2H,t); 3.22 (3H,s); 3.87 (2H,t); 4.21 (2H,t); 6.83 (2H,d); 6.90–7.40 (6H,complex); and 12.07 (1 H, broad, exchanges with D₂O).

PROCEDURE 7

3-[4-[2-[N-(2-Benzoxazolyl)-N-methylamino]ethoxy]phenyl]-N,N-dimethylpropanamide

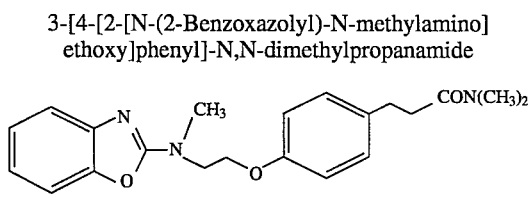

Triethylamine (0.4 mL) was added to an ice-cooled solution of 3-[4-[2-[N-(2-benzoxazolyl)-N-methylamino]ethoxy]phenyl]propanoic acid (1.00 g) in dry tetrahydrofuran (20 mL). The mixture was stirred at 0° C. during the addition of freshly distilled methyl chloroformate (0.25 mL), and stirring continued at this temperature for 45 minutes prior to the addition of a solution of dimethylamine in industrial methylated spirit (30% w/v; 20 mL). The mixture was stirred at room temperature for 20 hrs then evaporated. The residue was suspended in water (100 mL). Ethyl acetate (200 mL) and brine (100 mL) were added, the layers were separated and the aqueous layer extracted with ethyl acetate (2×200 mL). The combined ethyl acetate solutions were washed with brine (500 mL), dried (MgSO₄) and evaporated. The resulting gum was chromatographed on silica gel with 1% methanol in dichloromethane as eluent to afford a gum which crystallised on standing to afford the title compound, mp 103°–5° C.

¹H NMR δ (CDCl₃) 2.56 (2H,t); 2.91 (2H,t); 2.91 (2H,s); 2.93 (3H,s); 3.34 (3H,s); 3.93 (2H,t); 4.23 (2H,t); 6.80 (2H,d); and 6.90–7.35 (6H,complex).

PROCEDURE 8

Methyl 3-(4-benzyloxy)phenyl-2-(methylthio)propanoate

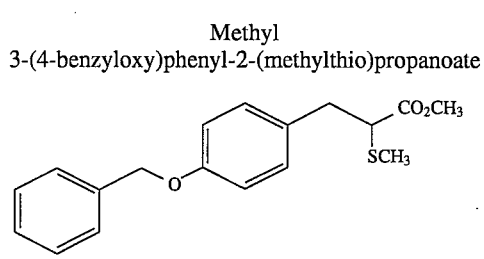

A solution of methyl 3-(4-benzyloxy)phenyl-2-chloropropanoate (*International Patent Appl., Publication No.* WO 9101337) (12.2 g) in methanol-tetrahydrofuran (1:1 v/v; 100 mL) was added to a stirred solution of sodium thiomethoxide (5.64 g) in methanol (50 mL) at room temperature. The mixture was stirred at room temperature for 30 minutes, refluxed for 3 hours then cooled and concentrated in vacuo. The residue was diluted with water (500 mL), extracted with ethyl acetate (3×500 mL) and the combined ethyl acetate layers washed with water (3×500 mL), brine (500 mL), dried (MgSO₄) and evaporated. The resulting gum was chromatographed on silica gel with dichloromethane as eluent to afford the title compound, mp 59°–60° C.

¹H NMR δ (CDCl₃) 2.15 (3H, s); 2.70–3.40 (3H, complex); 3.65 (3H, s); 5.00 (2H, s); 6.90 (2H, d); 7.15 (2H, d); and 7.40 (5H, s).

PROCEDURE 9

Methyl 3-(4-hydroxyphenyl)-2-(methylthio)propanoate

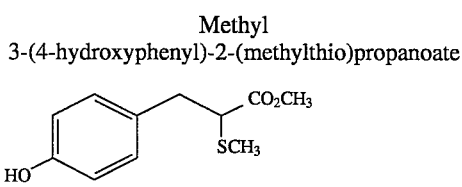

A solution of boron tribromide—dimethyl sulphide complex (14.9 g) in dichloromethane (200 mL) was added slowly to a stirred, ice-cooled solution of methyl 3-(4-benzyloxy)phenyl-2-(methylthio)propanoate (7.53 g) in dichloromethane (200 mL) under a nitrogen atmosphere. The mixture was warmed slowly to reflux, refluxed for a further 3 hours, then cooled and concentrated in vacuo. The residue was diluted with water (100 mL) and extracted with ethyl acetate (3×500 mL). The combined organic solutions were washed with water (3×500 mL), brine (500 mL), dried (MgSO₄) and evaporated. The residue was chromatographed on silica gel with 1% methanol in dichlormethane as eluent to afford the title compound, a gum which was used without further purification.

¹H NMR δ (CDCl₃) 2.17 (3H, s); 2.75–3.70 (3H, complex); 3.70 (3H, s); 5.20 (1H, broad, exchanges with D₂O); 6.70 (2H, d); and 7.07 (2H, d).

PROCEDURE 10

3-(4-Benzyloxy)phenyl-2-chloropropanamide

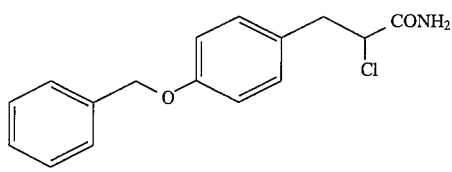

A mixture of methyl 3-(4-benzyloxy)phenyl-2-chloropropanoate (*International Patent Appl., Publication No.* WO 9101337) (12.0 g), tetrahydrofuran (240 mL), methanol (240 mL) and aqueous ammonia solution (specific gravity 0.88; 240 mL) was stirred at room temperature for 2.5 hrs. The organic solvents were evaporated in vacuo and the residue extracted with dichloromethane (3×600 mL). The combined dichloromethane solutions were washed with dilute hydrochloric acid solution (1 L), water (2×1 L) and brine (1 L), dried (MgSO$_4$) and evaporated. The residue was chromatographed on silica gel with 1% methanol in dichloromethane as eluent to afford the title compound, mp 131°–2° C.

$^1$H NMR δ (DMSO-d$_6$) 2.93 (1H, dd); 3.18 (1H, dd); 4.44 (1H, t); 5.06 (2H, s); 6.93 (2H, d); 7.15 (2H,d); 7.31 (1H, s, exchanges with D$_2$O); 7.31–7.50 (5H, complex); and 7.62 (1H, s, exchanges with D$_2$O).

PROCEDURE 11

3-(4-Benzyloxy)phenyl-2-(methylthio)propanamide

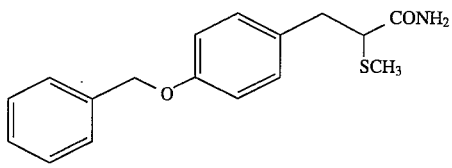

A mixture of 3-(4-benzyloxy)phenyl-2-chloropropanamide (9.9 g), sodium thiomethoxide (4.65 g), tetrahydrofuran (200 mL) and methanol (200 mL) was heated at reflux for 5 hrs, then allowed to stand at room temperature for a further 17.5 hrs before being concentrated in vacuo. The residue was diluted with water (1 L), extracted with dichloromethane (2×1 L) and the combined dichloromethane layers washed with water (3×1 L), brine (1 L), dried (MgSO$_4$) and evaporated. The residual solid was chromatographed on silica gel with 1% dichloromethane as eluent to afford the title compound, mp 108°–110° C.

$^1$H NMR δ (CDCl$_3$) 2.10 (3H, s); 2.88 (1H,dd); 3.22 (1H, dd); 3.38 (1H, t); 5.02 (2H, s); 5.84 exchanges with D$_2$O); 6.36 (1H, broad, exchanges with D$_2$O); 6.90 (2H, d); 7.15 (2H, d); and 7.25–7.50 (5H, complex).

PROCEDURE 12

3-(4-Hydroxyphenyl)-2-(methylthio)propanamide

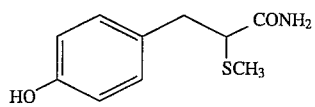

The title compound was prepared from 3-(4-benzyloxy)phenyl-2-(methylthio)propanamide (5.6 g) by a procedure similar to that described for Procedure 9.

$^1$H NMR δ (DMSO-d$_6$) 2.05 (3H, s); 2.65 (1H, dd); 2.99 (1H, dd); 3.30 (1H, dd); 6.64 (2H, d); 6.87 (1H, s, exchanges with D$_2$O); 6.98 (2H, d); 7.30 (1H, s, exchanges with D$_2$O); and 9.17 (1H, s, exchanges with D$_2$O).

PROCEDURE 13

2-[4-[2-[N-(2-Benzoxazolyl)-N-methylaminoethoxy]benzyl]perhydro-1,4-thiazin-3-one

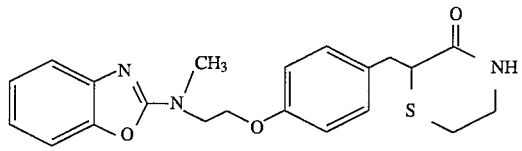

Method A

Sodium methoxide (0.62 g) was added portionwise to an ice cooled, stirred solution of aminoethanethiol hydrochloride (1.31 g) in methanol (10 mL), and the resulting slurry stirred at 0° C. for 10 minutes prior to the addition of a solution of methyl 3-[4-[2-[N-(2-benzoxazolyl)-N-methylamino]ethoxy]-phenyl]-2-bromopropanoate (1.25 g) in methanol (15 mL). The mixture was heated at reflux for 5 hrs, then cooled and stirred at room temperature for a further 18 hrs before being concentrated in vacuo. The residue was diluted with water (300 mL), extracted with ethyl acetate (3×100 mL) and the combined ethyl acetate layers washed with water (3×200 mL), brine (200 mL), dried (MgSO$_4$) and evaporated. The residue was chromatographed on silica gel with ethyl acetate as eluent to afford the title compound, a foam, mp 57°–63° C.

$^1$H NMR δ (CDCl$_3$) 2.70 (2H, complex); 2.90 (1H, dd); 3.34 (3H, s); 3.40 (1H, dd); 3.53 (2H, complex); 3.65 (1H,dd); 3.94 (2H, t); 4.25 (2H, t); 6.19 (1H, exchanges with D$_2$); 6.83 (2H, d); and 6.95–7.40 (6H, complex)

Method B

The title compound, identical with that prepared by Method A, was prepared from 2-(4-hydroxybenxyl)perhydro-1,4-thiazin-3-one by a procedure similar to that described in Procedure 1.

PROCEDURE 14

2-(4-Benzyloxybenzyl)perhydro-1,4-thiazin-3-one

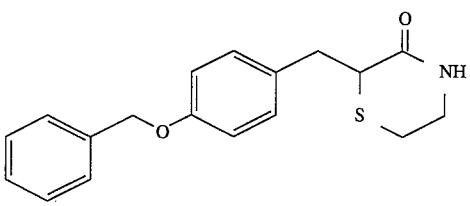

Methyl 3-(4-benzyloxy)phenyl-2-chloropropanoate (*International Patent Appl., Publication No.* WO 9101337) was reacted with aminoethanethiol hydrochloride in a manner analogous to that described in Procedure 1.3 (Method A). The crude product was chromatographed on silica gel with 1.5% methanol in dichloromethane as eluent to afford the title compound, mp 126°–8° C.

$^1$H NMR δ (CDCl$_3$) 2.65–3.10 (3H, complex); 3.40–3.80 (4H, complex); 5.07 (2H, s); and 6.90–7.60 (10H, complex, reduces to 9H on shaking with D$_2$O).

PROCEDURE 15

2-(4-Hydroxybenzyl)perhydro-1,4-thiazin-3-one

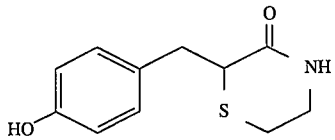

The title compound, a foam mp 50°–53° C., was prepared from 2-(4-benzyloxybenzyl)perhydro-1,4-thiazin-3-one by a procedure similar to that described in Procedure 9.

$^1$H NMR δ (CDCl$_3$: DMSO-d$_6$ 1:1 v/v) 2.40–2.80 (3H, complex); 3.05–3.70 (4H, complex); 6.67 (2H, d); 7.02 (2H, d); 7.75 (1H, broad, exchanges with D$_2$O); and 9.00 (1H, broad, exchanges with D$_2$O).

PROCEDURE 16

Methyl 2-(benzenesulphonyl)-3-(4-benzyloxyphenyl)propanoate

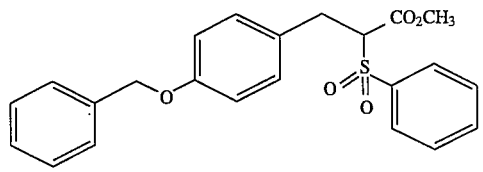

A mixture of methyl 3-(4-benzyloxyphenyl)-2-chloropropanoate (*International Patent Appl., Publication No.* WO 9101337) (0.50 g), sodium benzenesulphinate (0.29 g) and dry N,N-dimethylformamide (25 mL) was heated at 80° C. for 24 hrs. The mixture was cooled and diluted with water (500 mL), then extracted with dichloromethane (2×250 mL). The combined organic solutions were washed with water (2×250 mL) and brine (250 mL), dried (MgSO$_4$) and evaporated. The residue was chromatographed on silica gel with dichloromethane as eluent to afford the title compound.

$^1$H NMR δ (CDCl$_3$) 3.15 (1H, dd); 3.33 (1H, dd); 3.53 (3H, s); 4.17 (1H, dd); 5.00 (2H, s); 6.85 (2H, d); 7.03 (2H, d); and 7.25–7.90 (10H, complex).

PROCEDURE 17

Methyl 2-(benzenesulphonyl)-3-(4-hydroxyphenyl)propanoate

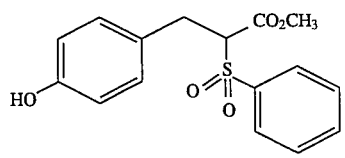

The title compound, a gum, was prepared from methyl 2-(benzenesulphonyl)-3-(4-benzyloxyphenyl)propanoate by a method similar to that described in Procedure 9.

$^1$H NMR δ (CDCl$_3$) 3.13 (1H, dd); 3.33 (1H, dd); 3.53 (3H, s); 4.16 (1H, dd); 4.82 (1H, s, exchanges with D$_2$O); 6.72 (2H, d); 6.98 (2H, d); 7.55–7.80 (3H, complex); and 7.90 (2H, d).

DEMONSTRATION OF EFFICACY OF COMPOUNDS

Obese Mice, Oral Glucose Tolerance Test

C57bl1/6 obese (ob/ob) mice were fed on powdered oxoid diet. After at least one week, the mice continued on a powdered oxoid diet or were fed powdered oxoid diet containing the test compound. After 8 days on the supplemented diet all of the mice were fasted for 5 hours prior to receiving an oral load of glucose (3 g/kg). Blood samples for glucose analysis were taken 0, 45, 90 and 135 minutes after glucose administration and the results appear below as the percentage reduction in area under the blood glucose curve where test compound treated groups are compared with the control groups. 8 mice were used for each treatment.

Activity table

| Example No. | Level in diet (μmol.kg$^{-1}$ of diet) | % Reduction in area under blood glucose curve |
| --- | --- | --- |
| 1 | 1000 | 45 |
| 2 | 1000 | 55 |
| 3 | 1000 | 58 |
| 4 | 3000 | 55 |
| 5 | 3000 | 42 |
| 6 | 1000 | 55 |
| 7 | 1000 | 51 |
| 8 | 1000 | 58 |
| 9 | 1000 | 58 |
| 10 | 1000 | 60 |
| 11 | 1000 | 60 |
| 13 | 3000 | 43 |
| 14 | 1000 | 45 |
| 15 | 3000 | 31 |
| 16 | 2000 | 49 |
| 17 | 3000 | 30 |
| 18 | 300 | 44 |
| 19 | 300 | 63 |
| 21 | 1000 | 27 |
| 22 | 3000 | 54 |
| 24 | 300 | 58 |
| 26 | 1000 | 65 |
| 28 | 1000 | 66 |
| 30 | 300 | 57 |
| 31 | 1000 | 50 |
| 32 | 1000 | 59 |

I claim:
1. A compound of formula (I):

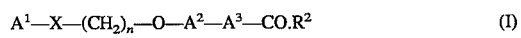

A$^1$—X—(CH$_2$)$_n$—O—A$^2$—A$^3$—CO.R$^2$  (I)

or a tautomeric form thereof and/or a pharmaceutically acceptable salt thereof, and/or a pharmaceutically acceptable solvate thereof, wherein:

A$^1$ represents a substituted or unsubstituted aromatic heterocyclyl group;

A$^2$ represents a benzene ring having three optional substituents;

A³ represents a moiety of formula —(CH₂)ₘ—CHR¹— wherein R¹ represents a halogen atom or a moiety of formula S(O)ₚA⁴ wherein A⁴ represents hydrogen, substituted or unsubstituted alkyl, aryl, aralkyl, alkylcarbonyl or an aromatic heterocyclyl group and p represents zero or an integer 1 or 2 and m represents zero or an integer in the range of from 1 to 5, or A³ represents a moiety of formula —CH=CR¹— wherein R¹ is as defined above;

R² represents OR³ wherein R³ represents hydrogen, alkyl, aryl or aralkyl, or R² represents —NR⁴R⁵ wherein R⁴ and R⁵ each independently represent hydrogen or alkyl or R⁴ and R⁵ together with the nitrogen atom to which they are attached form a heterocyclic ring;

X represents O, S or NR wherein R represents a hydrogen atom, an alkyl group, an acyl group, an aralkyl group wherein the aryl moiety may be substituted or unsubstituted, or a substituted or unsubstituted aryl group; and n represents an integer in the range of from 2 to 6.

2. A compound according to claim 1, wherein A¹ represents a moiety of formula (a), (b) or (c):

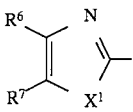

(a)

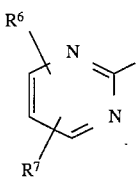

(b)

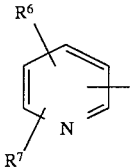

(c)

wherein:

R⁶ and R⁷ each independently represents a hydrogen or halogen atom, an alkyl or alkoxy group or a substituted or unsubstituted aryl group or when R⁶ and R⁷ are each attached to adjacent carbon atoms, then R⁶ and R⁷ together with the carbon atoms to which they are attached form a benzene ring wherein each carbon atom represented by R⁶ and R⁷ together may be substituted or unsubstituted; and in the moiety of formula (a), X¹ represents oxygen or sulphur.

3. A compound according to claim 1 wherein A³ represents —CH=CR¹—.

4. A compound according to claim 1 wherein A³ represents —(CH₂)ₘ—CHR¹.

5. A compound according to claim 1 wherein R¹ represents chlorine.

6. A compound according to any one of claims 1 to 4, wherein R¹ represents a moiety S(O)ₚA⁴.

7. A compound according to claim 4, wherein A⁴ is iso-propyl or phenyl.

8. A compound according to claim 1 wherein R² represents OR³.

9. A compound according to claim 1 wherein R³ represents hydrogen or alkyl.

10. A compound according to claim 1 selected from the group consisting of:

methyl 3-[4-[2-[N-(2-benzoxazolyl)-N-methylamino]ethoxy]phenyl]-2-chloropropanoate;

methyl 3-[4-[2-[N-(2-benzoxazolyl-N-methylamino]ethoxy]phenyl]-2-bromopropanoate;

methyl 3-[4-[2-[N-(2-benzoxazolyl)-N-methylamino]ethoxy]phenyl]-2-iodopropanoate;

methyl 3-[4-[2-[N-methyl-N-(2-pyridyl)amino]ethoxy]phenyl]-2-chloropropanoate;

methyl 4-[4-[2-[N-(2-benzoxazolyl)-N-methylamino]ethoxy]phenyl]-2-chlorobutanoate;

3-[4-[2-[N-(2-benzoxazolyl)-N-methylamino]ethoxy]phenyl]-2-chloropropanoic acid;

3-[4-[2-[N-(2-benzoxazolyl)-N-methylamino]ethoxy]phenyl]-2-chloropropanamide;

3-[4-[2-[N-(2-benzoxazolyl)-N-methylamino]ethoxy]phenyl]-2-chloro-N,N-dimethylpropanamide;

ethyl 3-[4-[2-[N-(2-benzoxazolyl)-N-methylamino]ethoxy]phenyl]-2-fluoropropanoate;

3-[4-[2-[N-(2-benzoxazolyl)-N-methylamino]ethoxy]phenyl]-2-fluoropropanoic acid;

3-[4-[2-[N-(2-benzoxazolyl)-N-methylamino]ethoxy]phenyl]-2-fluoropropanamide;

ethyl (E)-3-[4-[2-[N-(2-benzoxazolyl)-N-methylamino]ethoxy]-phenyl]-2-fluoropropenoate;

methyl 3-[4-[2-[N-(2-benzoxazolyl)-N-methylamino]ethoxy]phenyl]-2-(methylthio)propanoate;

3-[4-[2-[N-(2-benzoxazolyl)-N-methylamino]ethoxy]phenyl]-2(methylthio)propanoic acid;

3-[4-[2-[N-(2-benzoxazolyl)-N-methylamino]ethoxy]phenyl]-2-(methylthio)propanamide;

3-[4-[2-[N-(2-benzoxazolyl)-N-methylamino]ethoxy]phenyl]-2-mercaptopropanoic acid;

methyl 2-(acetylthio)-3-[4-[2-[N-(2-benzoxazolyl)-N-methylamino]ethoxy]phenyl]propanoate;

3-[4-[2-[N-(2-benzoxazolyl)-N-methylamino]ethoxy]phenyl]-2-(2-aminoethylthio)propanoic acid;

methyl 3-[4-[2-[N-(2-benzoxazolyl)-N-methylamino]ethoxy]phenyl]-2-(phenylthio)propanoate;

methyl 2-(benzenesulphonyl)-3-[4-[2-[N-(2-benzoxazolyl)-N-methylamino]ethoxy]phenyl]propanoate;

2-(benzenesulphonyl)-3-[4-[2-[N-(2-benzoxazolyl)-N-methylamino]ethoxy]phenyl]propanoic acid;

3-[4-[2-[N-(2-benzoxazolyl)-N-methylamino]ethoxy]phenyl]-2-(phenylthio)propanoic acid;

methyl 3-[4-[2-[N-(2-benzoxazolyl)-N-methylamino]ethoxy]phenyl]-2-(4-methylphenylthio)propanoate;

3-[4-[2-[N-(2-benzoxazolyl)-N-methylamino]ethoxy]phenyl]-2-(4-methylphenylthio)propanoic acid;

methyl 3-[4-[2-[N-(2-benzoxazolyl)-N-methylamino]ethoxy]phenyl]-2-(4-methoxyphenylthio)propanoate;

3-[4-[2-[N-(2-benzoxazolyl)-N-methylamino]ethoxy]phenyl]-2-(4-methoxyphenylthio)propanoic acid;

methyl 3-[4-[2-[N-(2-benzoxazolyl)-N-methylamino]ethoxy]phenyl]-2-(4-chlorophenylthio)propanoate;

3-[4-[2-[N-(2-benzoxazolyl)-N-methylamino]ethoxy]phenyl]-2-(4-chlorophenylthio)propanoic acid;

methyl 3-[4-[2-[N-(2-benzoxazolyl)-N-methylamino]ethoxy]phenyl-2-(2-propylthio)propanoate;

3-[4-[2-[N-(2-benzoxazolyl)-N-methylamino]ethoxy]phenyl]-2-(2-propylthio)propanoic acid;

3-[4-[2-[N-methyl-N-(2-pyridyl)amino]ethoxy]phenyl]-2-mercaptopropanoic acid; and methyl 3-[4-[2-[N-(2-benzoxazolyl)-N-methylamino]ethoxy]phenyl]-2-(2-pyridylthio)propanoate; or a tautomeric form thereof and/or a pharmaceutically acceptable salt thereof, and/or a pharmaceutically acceptable solvate thereof.

11. A pharmaceutical composition comprising an effective amount of the compound according to claim 1, or a tautomeric form thereof, or a pharmaceutically acceptable salt thereof, or a pharmaceutically acceptable solvate thereof, and a pharmaceutically acceptable carrier thereof.

12. A method for the treatment or prevention of hyperglycemia, hyperlipidemia, hypertension, cardiovascular disease and eating disorders in a human or non-human mammal which comprises administering an effective amount of the compound according to claim 1, or a tautomeric form thereof, or a pharmaceutically acceptable salt thereof, or a pharmaceutically acceptable solvate thereof to a human or non-human in need thereof.

* * * * *